(12) United States Patent
Choi et al.

(10) Patent No.: US 10,310,378 B2
(45) Date of Patent: *Jun. 4, 2019

(54) BLOCK COPOLYMER

(71) Applicant: LG Chem, Ltd., Seoul (KR)

(72) Inventors: Eun Young Choi, Daejeon (KR); No Jin Park, Daejeon (KR); Jung Keun Kim, Daejeon (KR); Je Gwon Lee, Daejeon (KR); Se Jin Ku, Daejeon (KR); Mi Sook Lee, Daejeon (KR); Hyung Ju Ryu, Daejeon (KR); Sung Soo Yoon, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/514,939

(22) PCT Filed: Sep. 30, 2015

(86) PCT No.: PCT/KR2015/010327
§ 371 (c)(1),
(2) Date: Mar. 28, 2017

(87) PCT Pub. No.: WO2016/053005
PCT Pub. Date: Apr. 7, 2016

(65) Prior Publication Data
US 2017/0247492 A1 Aug. 31, 2017

(30) Foreign Application Priority Data

Sep. 30, 2014 (KR) .................. 10-2014-0131964
Dec. 8, 2014 (KR) .................. 10-2014-0175400
(Continued)

(51) Int. Cl.
*G03F 7/004* (2006.01)
*G03F 7/16* (2006.01)
(Continued)

(52) U.S. Cl.
CPC ............ *G03F 7/165* (2013.01); *B05D 1/005* (2013.01); *B05D 3/007* (2013.01);
(Continued)

(58) Field of Classification Search
CPC ........ G03F 7/162; G03F 7/165; G03F 7/2004; G03F 7/40; G03F 7/039; G03F 7/0046;
(Continued)

(56) References Cited

U.S. PATENT DOCUMENTS 3,976,672 A 8/1976 Strunk et al.
5,115,056 A 5/1992 Mueller et al.
(Continued)

FOREIGN PATENT DOCUMENTS

CN 1333790 A 1/2002
CN 1337974 A 2/2002
(Continued)

OTHER PUBLICATIONS

CN Search Report for Application No. 201480071920.0 dated Aug. 2, 2017.
(Continued)

*Primary Examiner* — Amanda C. Walke
(74) *Attorney, Agent, or Firm* — Lerner, David, Littenberg, Krumholz & Mentlik, LLP

(57) ABSTRACT

The present application relates to a block copolymer and uses thereof. The present application can provide a block copolymer—which exhibits an excellent self-assembling property and thus can be used effectively in a variety of applications—and uses thereof.

15 Claims, 8 Drawing Sheets

(30) Foreign Application Priority Data

| Dec. 8, 2014 | (KR) | 10-2014-0175401 |
|---|---|---|
| Dec. 8, 2014 | (KR) | 10-2014-0175402 |
| Dec. 8, 2014 | (KR) | 10-2014-0175406 |
| Dec. 8, 2014 | (KR) | 10-2014-0175407 |
| Dec. 8, 2014 | (KR) | 10-2014-0175410 |
| Dec. 8, 2014 | (KR) | 10-2014-0175411 |
| Dec. 8, 2014 | (KR) | 10-2014-0175412 |
| Dec. 8, 2014 | (KR) | 10-2014-0175413 |
| Dec. 8, 2014 | (KR) | 10-2014-0175414 |
| Dec. 8, 2014 | (KR) | 10-2014-0175415 |
| Jun. 4, 2015 | (KR) | 10-2015-0079486 |

(51) Int. Cl.

| C08G 61/12 | (2006.01) |
|---|---|
| H01L 21/3105 | (2006.01) |
| H01L 21/027 | (2006.01) |
| C08F 212/08 | (2006.01) |
| C08F 216/12 | (2006.01) |
| C08F 220/10 | (2006.01) |
| C08F 220/26 | (2006.01) |
| C08F 220/30 | (2006.01) |
| C08J 5/18 | (2006.01) |
| C08L 53/00 | (2006.01) |
| B05D 1/00 | (2006.01) |
| B05D 3/00 | (2006.01) |
| C08F 293/00 | (2006.01) |
| C09D 153/00 | (2006.01) |
| G03F 7/09 | (2006.01) |
| G03F 7/039 | (2006.01) |
| G03F 7/20 | (2006.01) |
| C08F 32/06 | (2006.01) |
| C08F 299/02 | (2006.01) |
| C08G 61/08 | (2006.01) |
| C08F 2/14 | (2006.01) |
| C08J 7/12 | (2006.01) |
| G03F 7/00 | (2006.01) |
| G03F 7/30 | (2006.01) |
| C08L 53/02 | (2006.01) |
| B81C 1/00 | (2006.01) |
| B82Y 40/00 | (2011.01) |

(52) U.S. Cl.
CPC .......... B81C 1/00428 (2013.01); C08F 2/14 (2013.01); C08F 32/06 (2013.01); C08F 212/08 (2013.01); C08F 216/12 (2013.01); C08F 220/10 (2013.01); C08F 220/26 (2013.01); C08F 220/30 (2013.01); C08F 293/00 (2013.01); C08F 293/005 (2013.01); C08F 299/024 (2013.01); C08G 61/08 (2013.01); C08G 61/12 (2013.01); C08J 5/18 (2013.01); C08J 7/123 (2013.01); C08L 53/00 (2013.01); C08L 53/005 (2013.01); C08L 53/02 (2013.01); C09D 153/00 (2013.01); G03F 7/0002 (2013.01); G03F 7/0046 (2013.01); G03F 7/039 (2013.01); G03F 7/091 (2013.01); G03F 7/16 (2013.01); G03F 7/162 (2013.01); G03F 7/2004 (2013.01); G03F 7/30 (2013.01); H01L 21/0273 (2013.01); H01L 21/31055 (2013.01); H01L 21/31056 (2013.01); H01L 21/31058 (2013.01); B81C 2201/0149 (2013.01); B82Y 40/00 (2013.01); C01P 2002/70 (2013.01); C07B 2200/00 (2013.01); C08F 2220/301 (2013.01); C08F 2438/03 (2013.01); C08G 2261/1424 (2013.01); C08G 2261/1426 (2013.01); C08G 2261/332 (2013.01); C08G 2261/3324 (2013.01); C08G 2261/40 (2013.01); C08G 2261/418 (2013.01); C08J 2353/00 (2013.01)

(58) Field of Classification Search
CPC .......... C09D 153/00; H01L 21/0273; H01L 21/31055; H01L 21/31056; H01L 21/31058; C08L 53/00
USPC .......... 430/270.1, 322, 325, 329, 330, 331
See application file for complete search history.

(56) References Cited

U.S. PATENT DOCUMENTS

| 5,202,402 | A | 4/1993 | Funaki et al. |
|---|---|---|---|
| 5,234,604 | A | 8/1993 | Liao et al. |
| 5,391,626 | A | 2/1995 | Machida et al. |
| 5,418,290 | A | 5/1995 | Machida et al. |
| 5,554,695 | A | 9/1996 | Machida et al. |
| 5,728,431 | A | 3/1998 | Bergbreiter et al. |
| 6,314,225 | B1 | 11/2001 | Wang |
| 6,531,547 | B1 | 3/2003 | Visger et al. |
| 6,546,282 | B1 | 4/2003 | Inoue et al. |
| 6,953,649 | B2 | 10/2005 | Prat et al. |
| 7,538,159 | B2 | 5/2009 | Wang et al. |
| 8,163,189 | B2 | 4/2012 | Iyoda et al. |
| 8,211,737 | B2 | 7/2012 | Russell et al. |
| 8,791,042 | B2 | 7/2014 | Ronan et al. |
| 9,495,991 | B2 | 11/2016 | Han et al. |
| 2003/0143343 | A1 | 7/2003 | Kawabata et al. |
| 2004/0049836 | A1 | 3/2004 | Ashraf et al. |
| 2004/0110856 | A1 | 6/2004 | Young et al. |
| 2004/0143032 | A1 | 7/2004 | Auschra et al. |
| 2004/0242787 | A1 | 12/2004 | Chun et al. |
| 2006/0166033 | A1 | 7/2006 | Poetsch et al. |
| 2007/0142559 | A1 | 6/2007 | Wang et al. |
| 2007/0166648 | A1 | 7/2007 | Ponoth et al. |
| 2007/0219338 | A1 | 9/2007 | Takeda et al. |
| 2008/0105854 | A1 | 5/2008 | Huh et al. |
| 2008/0193658 | A1 | 8/2008 | Millward |
| 2008/0286333 | A1 | 11/2008 | Kangas et al. |
| 2008/0311402 | A1 | 12/2008 | Jung et al. |
| 2009/0114108 | A1 | 5/2009 | Oya et al. |
| 2009/0240001 | A1 | 9/2009 | Regner |
| 2009/0253867 | A1 | 10/2009 | Takahashi et al. |
| 2009/0306295 | A1 | 12/2009 | Mays et al. |
| 2010/0086801 | A1 | 4/2010 | Russell et al. |
| 2010/0098876 | A1 | 4/2010 | Hanson |
| 2010/0102415 | A1 | 4/2010 | Millward et al. |
| 2010/0120985 | A1 | 5/2010 | Konishi et al. |
| 2010/0155988 | A1 | 6/2010 | Keil et al. |
| 2010/0206057 | A1 | 8/2010 | Batchelder et al. |
| 2010/0210742 | A1 | 8/2010 | Iyoda et al. |
| 2010/0216312 | A1 | 8/2010 | Yamamoto et al. |
| 2010/0266957 | A1 | 10/2010 | Harada et al. |
| 2010/0285276 | A1 | 11/2010 | Kim et al. |
| 2010/0286351 | A1 | 11/2010 | Yoshida et al. |
| 2010/0305230 | A1 | 12/2010 | Li et al. |
| 2011/0186544 | A1 | 8/2011 | Endou et al. |
| 2011/0253946 | A1 | 10/2011 | Huh et al. |
| 2011/0294070 | A1 | 12/2011 | Hatakeyama et al. |
| 2012/0052446 | A1 | 3/2012 | Jaycox et al. |
| 2012/0116024 | A1 | 5/2012 | Lyoda et al. |
| 2012/0214094 | A1 | 8/2012 | Mikoshiba et al. |
| 2013/0078576 | A1 | 3/2013 | Wu et al. |
| 2013/0183828 | A1 | 7/2013 | Nakamura et al. |
| 2013/0189504 | A1 | 7/2013 | Nealey et al. |
| 2013/0209693 | A1 | 8/2013 | Vogel et al. |
| 2013/0209755 | A1 | 8/2013 | Hustad et al. |
| 2013/0248488 | A1 | 9/2013 | Han et al. |
| 2013/0284698 | A1 | 10/2013 | Ogihara |
| 2013/0306594 | A1 | 11/2013 | Hustad et al. |
| 2014/0011916 | A1 | 1/2014 | Lee et al. |
| 2014/0127456 | A1 | 5/2014 | Regner |
| 2014/0141375 | A1 | 5/2014 | Cho et al. |

(56) References Cited

U.S. PATENT DOCUMENTS

| | | |
|---|---|---|
| 2014/0238954 A1 | 8/2014 | Matsumiya et al. |
| 2014/0370442 A1 | 12/2014 | Ober et al. |
| 2015/0064630 A1 | 3/2015 | Wuister et al. |
| 2015/0085042 A1 | 3/2015 | Keoshkerian et al. |
| 2015/0197663 A1 | 7/2015 | Mizutani et al. |
| 2015/0228298 A1 | 8/2015 | Han et al. |
| 2016/0204653 A1 | 7/2016 | Lee |
| 2016/0257838 A1 | 9/2016 | Senzaki et al. |
| 2016/0280823 A1 | 9/2016 | Kim et al. |
| 2016/0280831 A1 | 9/2016 | Park et al. |
| 2016/0280832 A1 | 9/2016 | Kim et al. |
| 2016/0280833 A1 | 9/2016 | Lee et al. |
| 2016/0280834 A1 | 9/2016 | Kim et al. |
| 2016/0280835 A1 | 9/2016 | Lee et al. |
| 2016/0304653 A1 | 10/2016 | Kim et al. |
| 2016/0304654 A1 | 10/2016 | Lee et al. |
| 2016/0304655 A1 | 10/2016 | Lee et al. |
| 2016/0311958 A1 | 10/2016 | Kim et al. |
| 2016/0311959 A1 | 10/2016 | Lee et al. |
| 2016/0311960 A1 | 10/2016 | Lee et al. |
| 2016/0333221 A1 | 11/2016 | Mumtaz et al. |
| 2017/0008992 A1 | 1/2017 | Lee et al. |
| 2017/0058071 A1 | 3/2017 | Lee et al. |
| 2017/0210938 A1 | 7/2017 | Ku et al. |
| 2017/0219922 A1 | 8/2017 | Ku et al. |
| 2017/0226235 A1 | 8/2017 | Park et al. |
| 2017/0226258 A1 | 8/2017 | Lee et al. |
| 2017/0226260 A1 | 8/2017 | Lee et al. |
| 2017/0226261 A1 | 8/2017 | Lee et al. |
| 2017/0247492 A1 | 8/2017 | Choi et al. |
| 2017/0306074 A1 | 10/2017 | Lee et al. |
| 2017/0313869 A1 | 11/2017 | Lee et al. |
| 2018/0170023 A1 | 6/2018 | Park et al. |

FOREIGN PATENT DOCUMENTS

| | | |
|---|---|---|
| CN | 101215362 A | 7/2008 |
| CN | 101443371 A | 5/2009 |
| CN | 101492520 A | 7/2009 |
| CN | 101578232 A | 11/2009 |
| CN | 101688047 A | 3/2010 |
| CN | 101799626 A | 8/2010 |
| CN | 101977839 A | 2/2011 |
| CN | 102172491 A | 9/2011 |
| CN | 102439076 A | 5/2012 |
| CN | 102967918 A | 3/2013 |
| CN | 103025827 A | 4/2013 |
| CN | 103180783 A | 6/2013 |
| CN | 103289285 A | 9/2013 |
| CN | 103562245 A | 2/2014 |
| CN | 105899556 A | 8/2016 |
| CN | 105899557 A | 8/2016 |
| CN | 105899559 A | 8/2016 |
| CN | 105899560 A | 8/2016 |
| CN | 105934454 A | 9/2016 |
| CN | 105934456 A | 9/2016 |
| CN | 105960422 A | 9/2016 |
| CN | 105980342 A | 9/2016 |
| CN | 106459326 A | 2/2017 |
| EP | 1141056 B1 | 8/2010 |
| EP | 2781550 A1 | 9/2014 |
| EP | 3078654 A1 | 10/2016 |
| EP | 3078691 B1 | 10/2016 |
| EP | 3078692 A1 | 10/2016 |
| EP | 3078694 A1 | 10/2016 |
| EP | 3203497 A1 | 8/2017 |
| EP | 3214102 A1 | 9/2017 |
| EP | 3225641 A1 | 10/2017 |
| GB | 898065 A | 6/1962 |
| JP | 01260360 A | 10/1989 |
| JP | H01260360 A | 10/1989 |
| JP | H5320281 A | 12/1993 |
| JP | H0665333 A | 3/1994 |
| JP | H10237143 A | 9/1998 |
| JP | H10245427 A | 9/1998 |
| JP | H1143523 A | 2/1999 |
| JP | 2000053734 A | 2/2000 |
| JP | 2000281737 A | 10/2000 |
| JP | 2000285751 A | 10/2000 |
| JP | 3121116 B2 | 12/2000 |
| JP | 2001513125 A | 8/2001 |
| JP | 2001294617 A | 10/2001 |
| JP | 2002145973 A | 5/2002 |
| JP | 2003536105 A | 12/2003 |
| JP | 2004026688 A | 1/2004 |
| JP | 2004323773 A | 11/2004 |
| JP | 2005015508 A | 1/2005 |
| JP | 2005097442 A | 4/2005 |
| JP | 2005148205 A | 6/2005 |
| JP | 2005530030 A | 10/2005 |
| JP | 2005531618 A | 10/2005 |
| JP | 2007070453 A | 3/2007 |
| JP | 2007077292 A | 3/2007 |
| JP | 2007246600 A | 9/2007 |
| JP | 200855579 A | 3/2008 |
| JP | 2009057519 A | 3/2009 |
| JP | 200986354 A | 4/2009 |
| JP | 2009203439 A | 9/2009 |
| JP | 2010507803 A | 3/2010 |
| JP | 2010115832 A | 5/2010 |
| JP | 2010145158 A | 7/2010 |
| JP | 2010202723 A | 9/2010 |
| JP | 20100275349 A | 12/2010 |
| JP | 4625901 B2 | 2/2011 |
| JP | 2012001787 A | 1/2012 |
| JP | 2012012577 A | 1/2012 |
| JP | 2012093699 A | 5/2012 |
| JP | 2012174984 A | 9/2012 |
| JP | 201368882 A | 4/2013 |
| JP | 2013512323 A | 4/2013 |
| JP | 2013514449 A | 4/2013 |
| JP | 2013121430 A | 6/2013 |
| JP | 2013219334 A | 10/2013 |
| JP | 2013232501 A | 11/2013 |
| JP | 201412807 A | 1/2014 |
| JP | 2014070154 A | 4/2014 |
| JP | 2014102503 A | 6/2014 |
| JP | 2014162504 A | 9/2014 |
| JP | 2015000896 A | 1/2015 |
| JP | 2016539239 A | 12/2016 |
| JP | 2016540863 A | 12/2016 |
| JP | 2017502116 A | 1/2017 |
| JP | 2017505356 A | 2/2017 |
| JP | 2017530236 A | 10/2017 |
| JP | 2017530238 A | 10/2017 |
| JP | 2017533302 A | 11/2017 |
| KR | 20010101356 | 11/2001 |
| KR | 100622353 B1 | 9/2006 |
| KR | 20090015742 A | 2/2009 |
| KR | 100935863 B1 | 1/2010 |
| KR | 20100033962 A | 3/2010 |
| KR | 20100070380 A | 6/2010 |
| KR | 20100123920 A | 11/2010 |
| KR | 20110018678 A | 2/2011 |
| KR | 20110086834 A | 8/2011 |
| KR | 20110097707 A | 8/2011 |
| KR | 20110102998 A | 9/2011 |
| KR | 20110112501 A | 10/2011 |
| KR | 101102680 B1 | 1/2012 |
| KR | 20120119998 A | 11/2012 |
| KR | 20130094264 A | 8/2013 |
| KR | 20130113596 A | 10/2013 |
| KR | 20130128346 A | 11/2013 |
| KR | 20140063790 A | 5/2014 |
| KR | 20150066488 A | 6/2015 |
| KR | 20150067065 A | 6/2015 |
| KR | 20150067069 A | 6/2015 |
| KR | 20150067070 A | 6/2015 |
| KR | 20160038705 A | 4/2016 |
| TW | 201323461 | 6/2013 |
| TW | 201428046 A | 7/2014 |
| TW | 201536823 A | 10/2015 |
| TW | 201538548 A | 10/2015 |
| WO | 9837136 A1 | 8/1998 |

(56) References Cited

FOREIGN PATENT DOCUMENTS

| WO | 2007055371 A1 | 5/2007 |
|---|---|---|
| WO | 2012144735 A2 | 10/2012 |
| WO | 2013069544 A1 | 5/2013 |
| WO | 2013120051 A1 | 8/2013 |
| WO | 2013158527 A1 | 10/2013 |
| WO | 2014050905 A1 | 4/2014 |
| WO | 2014090178 A1 | 6/2014 |
| WO | 2014124795 A1 | 8/2014 |
| WO | 2015084121 A1 | 6/2015 |
| WO | 2015084122 A1 | 6/2015 |
| WO | 2015084123 A1 | 6/2015 |
| WO | 2015084124 A1 | 6/2015 |
| WO | 2015084125 A1 | 6/2015 |
| WO | 2015084126 A1 | 6/2015 |
| WO | 2015084127 A1 | 6/2015 |
| WO | 2015087005 A1 | 6/2015 |
| WO | 2016052994 A1 | 4/2016 |
| WO | 2016052999 A1 | 4/2016 |
| WO | 2016053005 A1 | 4/2016 |
| WO | 2016053007 A1 | 4/2016 |
| WO | 2016053011 A1 | 4/2016 |

OTHER PUBLICATIONS

CN Search Report for Application No. CN201480072884.X dated Aug. 3, 2017.
CN Search Report for Application No. CN2014800740447 dated Aug. 1, 2017.
Extended European Search Report for Application No. EP14867273 dated Aug. 10, 2017.
Mariana Beija et al: "Fluorescence Anisotropy of Hydrophobic Probes in poly(N-decylacrylamide) block-poly( N, N-diethylacrylamide) Block Copolymer Aqueous Solutions: Evidence of Premicellar Aggregates" Journal of Physical Chemistry Part B: Condensed Matter, Materials, Surfaces, Interfaces & Bi0physical, vol. 114, No. 31, Aug. 12, 2010 (Aug. 12, 2010), 9977-9986, XP055394763, US ISSN: 1520-6106, D0I: 10.1021/jp101613y* abstract * * Scheme 1, PDcA11-block-PDEA295; p. 9978 *.
Anonymous., "Solid surface energy data (SFE) for common polymers", surface-tension.de, Feb. 2017, Retreived from the Internet: URL:http://www.surface-tension.de/solid-surface-energy.htm, XP002775246.
Cummins et al., "Solvothermal Vapor Annealing of Lamellar Poly-(styrene)-block-poly(D,L-lactide) Block Copolymer Thin Films for Directed Self-Assembly Application", ACS Applied Materials & Interfaces, Mar. 2016, vol. 8, No. 12, pp. 8295-8304, XP055419698.
Extended European Search Report for Application No. EP14867808.9 dated Nov. 10, 2017.
Extended European Search Report for Application No. EP14868022.6 dated Nov. 6, 2017.
Extended European Search Report for Application No. EP14868320.4 dated Nov. 20, 2017.
Extended European Search Report for Application No. EP14868480.6 dated Nov. 2, 2017.
Hvilsted et al., "Novel Fluorinated Polymer Materials Based on 2,3,5,6-Tetrafluoro-4-methoxyystyrene" In: "Advances in Controlled/Living Radical Polymerization", American Chemical Society, Jun. 26, 2003, vol. 854, pp. 236-249, XP055421064.
Mahajan et al., "Synthesis and Characterization of Amphiphilic Poly(ethylene oxide)-block-poly(hexylmethacrylate Copolymers", Macromolecular Chemistry and Physics, Wiley-Vch Verlag, Weinheim, DE, Jan. 2003, vol. 204, pp. 1047-1055, XP003030406.
Pochan et al., "Morphologies of microphase-seperated conformationally asymmetric diblock copolymers", Journal of Polymer Science Part B: Polymer Physics, Nov. 2017, vol. 35, No. 16, pp. 2629-2643, XP055417266.
Zhuang et al., "Synthesis of A-B type block copolymers using 1-phenylethyl dithiobenzoate as Reversible Addition-Fragmentation Chain Transfer agent", Database CA [online], Chemical Abstracts Service, Columbus, OH, XP002775247.

Palacios et al., Constructing Robust and Functional Micropatterns on Polystyrene Surfaces by Using Deep UV Irradiation, American Chemical Society, Langmuir, 29(8) pp. 2756-2763, Feb. 2013.
Chinese Search Report for Application No. 2014800727599 dated Jan. 8, 2018.
Chinese Search Report for Application No. 2014800741401 dated Mar. 9, 2018.
Chinese Search Report for Application No. 201480074156.2 dated Apr. 3, 2018.
Supplementary European Search Report for EP15847157 dated Mar. 21, 2018.
U.S. Appl. No. 15/102,139, filed Jun. 6, 2016.
U.S. Appl. No. 15/102,149, filed Jun. 6, 2016.
U.S. Appl. No. 15/102,156, filed Jun. 6, 2016.
U.S. Appl. No. 15/173,670, filed Jun. 5, 2016.
U.S. Appl. No. 15/173,671, filed Jun. 5, 2016.
U.S. Appl. No. 15/173,673, filed Jun. 5, 2016.
U.S. Appl. No. 15/173,674, filed Jun. 5, 2016.
U.S. Appl. No. 15/173,676, filed Jun. 5, 2016.
U.S. Appl. No. 15/514,929, filed Mar. 28, 2017.
U.S. Appl. No. 15/514,959, filed Mar. 28, 2017.
U.S. Appl. No. 15/514,967, filed Mar. 28, 2017.
U.S. Appl. No. 15/515,290, filed Mar. 29, 2017.
U.S. Appl. No. 15/515,293, filed Mar. 29, 2017.
U.S. Appl. No. 15/515,432, filed Mar. 29, 2017.
U.S. Appl. No. 15/515,812, filed Mar. 30, 2017.
U.S. Appl. No. 15/515,818, filed Mar. 30, 2017.
U.S. Appl. No. 15/515,821, filed Mar. 30, 2017.
Akiba, Isamu, et al., "Self-Assembly of Amphiphilic Block Copolymers Containing Poly(n-octadecyl acrylate) Block in Aqueous Solution." IOP Conference Series: Materials Science and Engineering, 2010, vol. 14, No. 1, pp. 1-8.
Hua et al. "Temperature-induced phase-transitions of methoxyoligo(oxyethylene) styrene-based block copolymers in aqueous solution", Soft Matter, 2013, 9, 8897.
International Search Report from PCT/KR2014/012023, dated Mar. 10, 2015.
International Search Report from PCT/KR2014/012024, dated Mar. 17, 2015.
International Search Report from PCT/KR2014/012025, dated Mar. 17, 2015.
International Search Report from PCT/KR2014/012026, dated Mar. 17, 2015.
International Search Report from PCT/KR2014/012027, dated Mar. 17, 2015.
International Search Report from PCT/KR2014/012028, dated Mar. 17, 2015.
International Search Report from PCT/KR2014/012029, dated Mar. 17, 2015.
International Search Report from PCT/KR2014/012030, dated Mar. 17, 2015.
International Search Report from PCT/KR2014/012031, dated Feb. 12, 2015.
International Search Report from PCT/KR2014/012032, dated Feb. 12, 2015.
International Search Report from PCT/KR2014/012033, dated Feb. 12, 2015.
International Search Report from PCT/KR2014/012034, dated Feb. 12, 2015.
International Search Report from PCT/KR2014/012035, dated Feb. 12, 2015.
International Search Report from PCT/KR2014/012036, dated Mar. 17, 2015.
International Search Report from PCT/KR2015/010313, dated Nov. 23, 2015.
International Search Report from PCT/KR2015/010320, dated Jan. 13, 2016.
International Search Report from PCT/KR2015/010322, dated Jan. 13, 2016.
International Search Report from PCT/KR2015/010323, dated Jan. 13, 2016.
International Search Report from PCT/KR2015/010327, dated Jan. 12, 2016.

(56) References Cited

OTHER PUBLICATIONS

International Search Report from PCT/KR2015/010330 dated Jan. 11, 2016.
International Search Report from PCT/KR2015/010332 dated Jan. 13, 2016.
International Search Report from PCT/KR2015/010334, dated Jan. 13, 2016.
International Search Report from PCT/KR2015/010335 dated Jan. 13, 2016.
International Search Report from PCT/KR2015/010338 dated Jan. 14, 2016.
IPO Search Report from Taiwan Application No. 103142745, dated Dec. 14, 2015.
IPO Search Report from Taiwan Application No. 103142777, dated Dec. 15, 2015.
IPO Search Report from Taiwan Application No. 103142780, dated Dec. 15, 2015.
IPO Search Report from Taiwan Application No. 103142784, dated Jan. 27, 2016.
IPO Search Report from Taiwan Application No. 103142786, dated Jan. 11, 2016.
IPO Search Report from Taiwan Application No. 103142790, dated Dec. 15, 2015.
IPO Search Report from Taiwan Application No. 103142794, dated Dec. 15, 2015.
IPO Search Report from Taiwan Application No. 103142798, dated Dec. 16, 2015.
IPO Search Report from Taiwan Application No. 103142805, dated Dec. 11, 2015.
IPO Search Report from Taiwan Application No. 103142955, dated Jan. 15, 2016.
IPO Search Report from Taiwan Application No. 103142956 dated Jan. 20, 2016.
IPO Search Report from Taiwan Application No. 103142963, dated Dec. 10, 2015.
IPO Search Report from Taiwan Application No. 104132186, dated Aug. 18, 2016.
IPO Search Report from Tawain Application No. 103142782, dated Dec. 11, 2015.
Khazimullis et al. "Gel formation in a mixture of a block copolymer and a nematic liquid crystal", Physical Review E 84, 021710 (2011).
Park et al., "Block Copolymer Lithography: Periodic Arrays of ~10 11 Holes in 1 Square Centimeter", Science 276, p. 1401-1404, May 30, 1997.
Tenneti et al. "Competition between liquid crystallinity and block copolymer self-assembly in core-shell rod-coil block copolymers", Soft Matter, 2008, 4, 458-461 (2008).
Tenneti et al. Hierarchical Nanostructures of Mesogen Jacketed Bent-Core Liquid Crystalline Block Copolymers, Proceedings Published 2007 by the American Chemical Society.
U.S. Appl. No. 15/101,794, filed Jun. 3, 2016.
U.S. Appl. No. 15/101,812, filed Jun. 3, 2016.
U.S. Appl. No. 15/101,827, filed Jun. 3, 2016.
U.S. Appl. No. 15/101,915, filed Jun. 5, 2016.
U.S. Appl. No. 15/102,089, filed Jun. 6, 2016.
U.S. Appl. No. 15/102,112, filed Jun. 6, 2016.
Chinese Search Report for Application No. 201480072759.9 dated Jan. 24, 2018.
Chinese Search Report for CN Application No. 201480071920.0, dated May 4, 2018.
Chinese Search Report for CN Application No. 201480072800.2, dated Apr. 10, 2018.
Chinese Search Report for CN Application No. 201480074045.1, dated Apr. 11, 2018.
Extented European Seach Report including Written Opinion for EP Application No. 15847574.9, dated May 3, 2018.
Extented European Search Report including Written Opinion for EP Application No. 15845928.9, dated May 2, 2018.
Extended European Search Report including Written Opinion for EP Application No. 15847598.8, dated May 11, 2018.
Extended European Search Report including Written Opinion for EP15845720.0 dated May 4, 2018.
Extended European Search Report with Written Opinion for EP158468322 dated May 3, 2018.
Funk, L. et al., "Novel Amphiphilic Styrene-Based Block Copolymers for Induced Surface Reconstruction," Macromolecular Chemistry and Physics, vol. 209, No. 1, Jan. 4, 2008, pp. 52-63, XP055382259, DE, ISSN: 1022-1352, DOI: 10.1002/macp.200700312.
Haeng-Dong Koh et al., "Location-controlled parallel and vertical orientation by dewetting-induced block copolymer directed self-assembly," Journal of Materials Chemistry C: Materials for Optical and Electronic Devices, vol. 1, No. 25, Jan. 1, 2013, pp. 4020-4024 XP055469744.
Ma J et al., "Synthesis and Solution-State Assembly or Buld State Thiol-ene Crosslinking of Pyrrolidinone- and Alkene-Functionalized Amphiphilic Block Fluorocopoplymers: From Functional Nanoparticles to Anti-Fouling Coatings", Australian Journal of Chemistry: An International Journal for Chemical Sci, Jan. 1, 2010, pp. 1159-1163, vol. 63, No. 8,C S I R O Publishing, Australia.
Mori H. et al., "Synthesis and Surface Characterization of Hydrophilic-Hydrophobic Block Copolymers Containing Poly(2,3-dihydroxypropyl methacrylate)," Macromolecules, American Chemical Society, US, vol. 27, No. 15, Jul. 18, 1994, pp. 4093-9297; XP000456650, DOI: 10.2021/MA00093A010.
Segalman R.A. et al., "Graphoepitaxy of Spherical Domain Block Copolymer Films," Advanced Materials, Wiley—VCH Verlag GmbH & Co. KGAA, DE, vol. 13, No. 15, Aug. 3, 2001, pp. 1152-1155; XP001129643, ISSN: 0935-9648, DOI: 10.1002/1521-4095(200108)13:15<1152: AID-A DMA1152>3.0.CO; 2-5.
Riedel et al., Synthesis, post-modification and self-assembled thin films of pentafluorostyrene containing block copolymers, European Polymer Journal 47 (2011) 675-684.
Yoshida, E. et al. Polymer Journal vol. 31 (5) pp. 429-434 (1999). Database CA [Online] Chemical Abstracts Service Ohi0 US; Zou, Yue: "Fluorosurfactant capable of preventing unevenness in photoresist coating and its preparation by anionic polymerization", XP002771143 retrieved from STN Database accession No. 2011:1148166 * abstract * & CN 102 172 491 A (Jiangsu Johnny Material Technology Co Ltd) Sep. 7, 011 (Sep. 7, 2011) Columbus, No. 2011:1148166.
European Search Report for Application No. EP14867501 dated Jul. 14, 2017.
Kago K et al: "X-ray reflectivity of polymer assembly at air-water interface" Supramolecular Science Butterworth-Heinemann Oxford GB vol. 5 No. 3-4, Jul. 1, 1998 (Jul. 1, 1998)pp. 349-355 XP027388373 ISSN: 0968-5677 [retrieved on Jul. 1, 1998] * abstract *.
Lutz Funk et al: "Novel Amphiphilic Styrene-Based Block Copolymers for Induced Surface Reconstruction". Macromolecular Chemistry and Physics., vol. 209, No. 1, Jan. 4, 2008 (Jan. 4, 2008), XP055382259 DE ISSN: 1022-1352 DOI: 10.1002/macp.200700312 * scheme 1, monomers M1, M4 table 2*.
Mori H et al: "Synthesis and Surface Characterization of Hydrophilic-Hydrophobic Block Copolymers Containing Poly(2, 3-Dihydroxypropyl Methacrylate)"Macromolecules American Chemical Society US vol. 27 No. 15 Jul. 18, 1994 (Jul. 18, 1994) pp. 4093-4100 XP000456650 ISSN: 0024-9297 D01: 10.10211MA00093A010 * abstract *.
EESR for EP Application No. 15847536.8 dated Aug. 23, 2018, 6 pages.
Beng H. Tan et al., "Synthesis and Self-Assembly of pH-Responsive Amphiphilic Poly (dimethylaminoethylmethacrylate)-block-Poly(pentafluorostyrene) Block Copolymer in Aqueous Solution", Macromolecular Rapid Communications, Jun. 17, 2009, vol. 30 (12), pp. 1002-1008.
C.M. Bates et al., Polymeric Cross-Linked Surface Treatments for Controlling Block Copolymer Orientation in Thin Films , Langmuir Article, American Chemical Society, Jan. 7, 2011, vol. 27, No. 5, pp. 1-7.
Chakrabarty, et al., "Tailor-Made Polyfluoroacrylate and its Block Copolymer by RAFT Polymerization in Miniemulsion; Improved Hydrophobicity in the Core-Shell Block Copolymer", Journal of Colloid and Interface Science, vol. 408, Oct. 2013, pp. 66-74.

(56) References Cited

OTHER PUBLICATIONS

Chinese Search Report for CN Application No. 2014800740447 dated Jun. 7, 2018, completed May 30, 2018.
Extended European Search Report including Written Opinion for Application No. EP15845665.7 dated Jun. 27, 2018.
Frank S. Bates et al., "Block Copolymer Thermodyanmics: Theory and Experiment", Annu. Rev. Phys. Chem., Oct. 1990, vol. 41 (1), pp. 525-557.
G.R. Strobl, "The Physics of Polymers: Concepts for Understanding Their Structures and Behavior", Springer (Abstract Only).
Gregory, et al., "Complex Polymer Architectures via RAFT Polymerization: From Fundamental Process to Extending the Scope Using Click Chemistry and Nature's Building Blocks", Progress in Polymer Science, vol. 37, No. 1, Jan. 2012, pp. 38-105.
Katja Nilles et al., "RAFT Polymerization of Activated 4-Vinylbenzoates"., Journal of Polymer Science: Part A: Polymer Chemistry, Jan. 1, 2009, vol. 47, pp. 1696-1705.
S. Chavda et al., "Synthesis of stimuli responsive PEG47-b-PAA126-b-PSt32 triblock copolymer and its self-assembly in aqueous solutions", European Polymer Journal, Sep. 2012, vol. 49, pp. 209-216.
Sachin Borkar et al., "New Highly Fluorinated Styrene-Based Materials with Low Surface Energy Prepared by ATRP", Macromolecules, Jan. 2004, vol. 37, pp. 788-794.
Truelsen et al., "Synthesis by ATRP of triblock copolymers with densely grafted styrenic end blocks from a polyisobutylene macroinitiator", Marcomol. Rapid. Commun., Jul. 2, 1999, vol. 21, No. 2, pp. 1-5.

BLOCK COPOLYMER

CROSS-REFERENCE TO RELATED APPLICATIONS

The present application is a national phase entry under 35 U.S.C. § 371 of International Application No. PCT/KR2015/010327, filed Sep. 30, 2015, published in Korean, which claims priority to and the benefit of Korean Patent Application Nos. 2014-0131964, filed on Sep. 30, 2014, No. 2015-0079486, filed on Jun. 4, 2015, No. 2014-0175411, filed on Dec. 8, 2014, No. 2014-0175414, filed on Dec. 8, 2014, No. 2014-0175410, filed on Dec. 8, 2014, No. 2014-0175415, filed on Dec. 8, 2014, No. 2014-0175412, filed on Dec. 8, 2014, No. 2014-0175413, filed on Dec. 8, 2014, No. 2014-0175407, filed on Dec. 8, 2014, No. 2014-0175406, filed on Dec. 8, 2014, No. 2014-0175400, filed on Dec. 8, 2014, No. 2014-0175401, filed on Dec. 8, 2014, and No. 2014-0175402, filed on Dec. 8, 2014, the disclosures of which are incorporated herein by reference in their entirety.

FIELD

The present application relates to a block copolymer and uses thereof.

BACKGROUND

The block copolymer has a molecular structure in which polymer blocks each with a distinct chemical structure are connected to one another by covalent bonds. The block copolymer can be constructed in a structure such as a sphere, a cylinder and a lamella through phase separation. The structure that is formed as the result of the self-assembly phenomenon of a block copolymer has a domain whose size can be adjusted, and it can be constructed in various forms which can be applied to the production of a variety of next-generation nanodevices, magnetic storage media, and patterns (by lithography or the like): to be specific, the production of high-density magnetic recording media, nanowires, quantum dots, metal dots or the like.

DESCRIPTION

Object

The present application provides block copolymers, polymer films, methods of forming a polymer film, and methods of forming a pattern.

Solution

An exemplary block copolymer may contain a block 1 and a block 2, which is different from the block 1. Each block in the block copolymer may be made up only of one type of a monomer, or it may be made up of two or more types of monomers. The block copolymer may be a diblock copolymer which contains each one of the block 1 and block 2 only, or it may be a triblock or multiblock (with more than three types of blocks) copolymer which contains 2 or more of either one or both of the block 1 and block 2 either exclusively or together with another type(s) of block(s).

A block copolymer contains 2 or more polymer chains which are connected to one another by one or more covalent bonds, and thus phase separation occurs. The following block copolymer of the present application can form a nanoscale structure through microphase separation. The form or size of such a nanoscale structure may be controlled, for example, by the size (i.e. molecular weight or the like) of the block copolymer or relative ratios among the blocks. The inventors recognized that the following block copolymer of the present application can form a cylindrical structure with high efficiency, especially by self-assembly.

For example, in the block copolymer of the present application, X that is calculated by the following Equation 1 may be in the range of 2.5 to 10 or 1.1 to 1.7.

$$X = 1 + (D \times M)/(K \times L) \quad \text{[Equation 1]}$$

In Equation 1, D represents the ratio (D2/D1) of the density (D2) of the second block to the density (D1) of the first block; M represents the ratio (M1/M2) of the molar mass (M1) of the first block to the molar mass (M2) of the second block; K represents the ratio (A2/A1) in a $^1$H-NMR spectrum of the area (A2) of the peak that is produced based on the second block to the area (A1) of the peak that is produced based on the first block; and L represents the ratio (H1/H2) of the number (H1) of hydrogen atoms in 1 mole of the repeat unit of the first block to the number (H2) of hydrogen atoms in 1 mole of the repeat unit of the second block.

There is no particular limitation to the method of conducting $^1$H-NMR to obtain the value of K that is substituted in Equation 1, and any method well known in the art can be used. One example of the above method is described in the example section below in the present specification. The method of calculating a peak area from the NMR result is well known in the art. For example, the peak area can be simply calculated when, by looking at the NMR result, the peaks derived from each of the block 1 and block 2 do not overlap each other; in contrast, when the peaks overlap each other, the ratio of the peaks is calculated, taking the overlapped part into consideration. There are various interpretation programs known in the field to calculate a peak area through an interpretation of a $^1$H-NMR spectrum; for example, a MestReC program can be used to calculate a peak area.

The density of each block of a block copolymer, which is required to obtain the value of D that is substituted in Equation 1, can be measured by using a buoyancy method that is well known in the art. For example, the density can be measured by analyzing the mass of the block copolymer that is immersed in a solvent—such as ethanol—whose mass and density in air are known. The density of a block can be measured, for example, by subjecting a homopolymer—that is made up only of the monomer that constitutes the above block—to a buoyancy method.

As described above, the value of M that is substituted in Equation 1 corresponds to the ratio of molar masses of repeat units of blocks in a block copolymer. The molar masses can be obtained in any method that is well known in the art; for example, the value of M can be obtained as the ratio of molar masses of monomers that make up blocks in a block copolymer. In this case, when any one of the blocks in the block copolymer is made up of two or more types of monomers, the molar mass of the monomer that is most abundant (in terms of number of moles)—among the above two or more types of monomers—in the above block can substitute for the value of the molar mass that is required to calculate the value of M.

As described above, the value of L that is substituted in Equation 1 block copolymer corresponds to the ratio of number of hydrogen atoms that 1 mole of block repeat units of a block copolymer contains. The above ratio can also be obtained based on the chemical structure of each repeat unit;

for example, the ratio can be obtained from the number of hydrogen atoms in the chemical structure of the monomer constituting each block of a block copolymer or by $^1$H-NMR. Also in this case, when any one of the blocks in a block copolymer is made up of two or more types of monomers, the molar mass of the monomer that is most abundant (in terms of number of moles)—among the above two or more types of monomers—in the above block can substitute for the value of the molar mass that is required to calculate the value of L.

Unless specifically indicated otherwise, the properties (e.g. density) that may change depending on the temperature in the present application are numerical values that are measured at room temperature. The term "room temperature" refers to the temperature in its natural state, which has not undergone heating or cooling, and may refer to a temperature of about 10° C. to 30° C., about 25° C., or about 23° C.

The X of Equation 1 is a numerical value that represents the amount ratio between the block 1 and block 2 in a block copolymer. The proportion of each block in a block copolymer is normally measured based on the molecular weight that is obtained based on gel permeation chromatography (GPC) or the like. However, the inventors recognized that, with the above general method being used, the ratio among the blocks was not correctly reflected and, thus, the method failed to realize the block copolymer as originally designed. For example, GPC alone cannot identify the occasional failure in the synthesis of a block copolymer (which contains each of its blocks to a respective target level) that occurs depending on the reactivity of the macroinitiator and monomers when the synthesis is intended by using any one block of the block copolymer as the macroinitiator as will be described below in the present specification.

In another example, the X of Equation 1 may be in the range of 2.5 to 6.7, 2.5 to 5, 2.8 to 5, or 3.3 to 5.

In still another example, the X of Equation 1 may be about 1.1 to 1.45, 1.1 to 1.35, 1.1 to 1.33, or 1.1 to 1.25.

For example, when the block 1 is—as will be described below in the present specification—either a block having an aromatic structure without a halogen atom and is contained in a block copolymer together with the block 2 that has an aromatic structure substituted in part by one or more halogen atoms or a block having a side chain and is contained in a block copolymer together with the block 2 that contains one or more halogen atoms, the block copolymer with the X ranging from 2.5 to 10 can form a structure in which the block 2 has a cylindrical form and is present inside the domain that is formed by the block 1, while the block copolymer with the X ranging from 1.1 to 1.7 can form a structure in which the block 1 has a cylindrical form and is present inside the domain that is formed by the block 2.

In the present application, the term "a side chain" refers to a chain that is connected to the main chain of a polymer, and the term "a chain-forming atom" refers to an atom that forms the above side chain of a block copolymer and, in other words, an atom that forms a linear structure of the side chain. The side chain may be a linear-type or a branched-type, but the number of chain-forming atoms is counted only by the number of atoms that form the longest linear chain, and the other atoms that are bonded to the above chain-forming atoms (e.g. when the chain-forming atom is a carbon atom, the hydrogen atom or the like that is bonded to the carbon atom) are not taken into account. For example, in the case of a branched-type chain, the number of chain-forming atoms may be counted by the number of chain-forming atoms that form the longest chain. For example, when the side chain is an n-pentyl group, all of the chain-forming atoms are carbon and the number of the chain-forming atoms is five, and also when the side chain is a 2-methylpentyl group, all of the chain-forming atoms are carbon and the number of the chain-forming atoms is 5. Examples of a chain-forming atom may include carbon, oxygen, sulfur, and nitrogen; a suitable chain-forming atom may be any one of carbon, oxygen and nitrogen, or any one of carbon and oxygen. The number of chain-forming atoms in a chain may be 8 or more, 9 or more, 10 or more, 11 or more, or 12 or more. The number of chain-forming atoms in a chain may also be 30 or less, 25 or less, 20 or less, or 16 or less.

The number average molecular weight (Mn) of the above block copolymer may be, for example, in the range of 3,000 to 300,000. In the present specification, the term "number average molecular weight" refers to a numerical value that is measured with GPC and calibrated based on a standard polystyrene, and, unless specifically indicated otherwise, the term "molecular weight" in the present specification refers to number average molecular weight. In another example, Mn may be, for example, 3000 or more, 5000 or more, 7000 or more, 9000 or more, 11000 or more, 13000 or more, or 15000 or more. In still another example, Mn may be about 250000 or less, 200000 or less, 180000 or less, 160000 or less, 140000 or less, 120000 or less, 100000 or less, 90000 or less, 80000 or less, 70000 or less, 60000 or less, 50000 or less, 40000 or less, 30000 or less, or 25000 or less. A block copolymer may have a polydispersity (Mw/Mn) in the range of 1.01 to 1.60. In another example, the Mw/Mn may be about 1.1 or more, about 1.2 or more, about 1.3 or more, or about 1.4 or more.

In such a range, a block copolymer can exhibit a sufficient self-assembling property. The Mn and the like of a block copolymer can be adjusted in consideration of the self-assembled structure of interest and the like.

The structure of the above block copolymer may be controlled to secure the self-assembly or phase separation property at a sufficient level. For example, either one or both of the block 1 and block 2 of a block copolymer that satisfies one or more of the aforementioned parameters may include at least an aromatic structure. Both the block 1 and block 2 may each include an aromatic structure; in this case, the aromatic structure included in any one of the block 1 or block 2 may be identical to or different from the aromatic structure in the other type of block. In addition, at least one among the block 1 and block 2 of a block copolymer that satisfies one or more of the aforementioned parameters may contain an aforementioned side chain or one or more halogen atoms which will be described below in the present specification, and the side chain and halogen atom(s) may be substituted for one or more parts of the above aromatic structures. The block copolymer of the present application may contain two or more blocks.

As described above, the block 1 and/or block 2 of the above block copolymer may each include an aromatic structure. The aromatic structure is included in either one or both of the block 1 and block 2. When each of the two types of blocks includes an aromatic structure, the aromatic structure included in one type of block may be identical to or different from that in the other type of block.

Unless specifically indicated otherwise, the term "an aromatic structure", "an aryl group" or "an arylene group" in the present specification may refer to a monovalent or divalent residue, which is a structure derived from a compound that includes a benzene ring, or two or more benzene rings connected to one another (either by sharing one or two carbon atoms or by any linker) or from a derivative of the above compound. The above aryl group or arylene group may refer to an aryl group with, for example, 6 to 30 carbons, 6 to 25 carbons, 6 to 21 carbons, 6 to 18 carbons, or 6 to 13 carbons. Examples of an aryl group or arylene group may also include a monovalent or divalent residue that is derived from benzene, naphthalene, azobenzene, anthracene, phenanthrene, tetracene, pyrene, benzopyrene or the like.

The above aromatic structure may be included in the main chain of a block or connected (in the form of a side chain) to the main chain of the block. The aforementioned parameter(s) may be controlled by controlling the aromatic structure that can be included in each block.

For example, the aforementioned parameter(s) can be controlled by including, in the block 1 of a block copolymer, a chain with 8 or more chain-forming atoms as a side chain to the block. The terms "a chain" and "a side chain" may refer to a common object in the present specification. In the case that the block 1 includes an aromatic structure, the above chain may be connected to the aromatic structure.

As mentioned above, a side chain may be a chain that contains 8 or more, 9 or more, 10 or more, 11 or more or 12 or more chain-forming atoms. The number of the chain-forming atoms in a side chain may also be 30 or less, 25 or less, 20 or less, or 16 or less. Each of the chain-forming atoms may be any one of carbon, oxygen, nitrogen and sulfur, or it may suitably be any one of carbon and oxygen.

A hydrocarbon chain such as an alkyl group, an alkenyl group and an alkynyl group may be exemplified as the side chain. At least one carbon atom in the above hydrocarbon chain may be substituted each by a sulfur atom, an oxygen atom, or a nitrogen atom.

When the side chain is connected to an aromatic structure, the chain may be connected to the aromatic structure either directly or by a linker. Examples of the linker may include an oxygen atom, a sulfur atom, $-NR_1-$, $-S(=O)_2-$, a carbonyl group, an alkylene group, an alkenylene group, an alkynylene group, $-C(=O)-X_1-$ and $-X_1-C(=O)-$, where the $R_1$ may represent a hydrogen atom, an alkyl group, an alkenyl group, an alkynyl group, an alkoxy group or an aryl group, and the $X_1$ may represent a single bond, an oxygen atom, a sulfur atom, $-NR_2-$, $-S(=O)_2-$, an alkylene group, an alkenylene group or an alkynylene group, where the $R_2$ may represent a hydrogen atom, an alkyl group, an alkenyl group, an alkynyl group, an alkoxy group, or an aryl group. An oxygen atom may be exemplified as a suitable linker. The side chain may be connected to an aromatic structure, for example, by an oxygen atom or a nitrogen atom.

When an aromatic structure is connected (in the form of a side chain) to the main chain of a block, the above aromatic structure may also be connected to the main chain either directly or by a linker. In this case, examples of the linker may include an oxygen atom, a sulfur atom, $-S(=O)_2-$, a carbonyl group, an alkylene group, an alkenylene group, an alkynylene group, $-C(=O)-X_1-$ or $-X_1-C(=O)-$, where the $X_1$ may represent a single bond, an oxygen atom, a sulfur atom, $-S(=O)_2-$, an alkylene group, an alkenylene group or an alkynylene group. Examples of a suitable linker that connects an aromatic structure to the main chain may include, but are not limited to, $-C(=O)-O-$ and $-O-C(=O)-$.

In another example, the aromatic structure that is included in the block 1 and/or block 2 of a block copolymer may contain 1 or more, 2 or more, 3 or more, 4 or more or 5 or more halogen atoms. The number of the halogen atoms may also be, for example, 30 or less, 25 or less, 20 or less, 15 or less, or 10 or less. Examples of the halogen atom may include fluorine and chlorine, and it may be advantageous to use fluorine. Such a block that includes an aromatic structure with one or more halogen atoms can efficiently realize a phase-separated structure by having sufficient interactions with (an)other block(s).

An exemplary aromatic structure that contains one or more halogen atoms may be an aromatic structure with 6 to 30 carbons, 6 to 25 carbons, 6 to 21 carbons, 6 to 18 carbons or 6 to 13 carbons, although it is not limited thereto.

When both the block 1 and block 2 of a block copolymer include an aromatic structure, to realize a sufficient level of phase separation in the structure, the block 1 may be set to include an aromatic structure without a halogen atom while the block 2 is set to include an aromatic structure with one or more halogen atoms. In addition, the aforementioned side chain may be connected to the aromatic structure of the above block 1, either directly or by a linker that contains oxygen or nitrogen.

When a block copolymer contains a block with a side chain, the block may be, for example, a block that is represented by the following Structural Formula 1.

[Structural Formula 1]

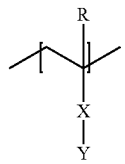

In Structural Formula 1, R represents a hydrogen atom or an alkyl group with 1 to 4 carbons; X represents a single bond, an oxygen atom, a sulfur atom, $-S(=O)_2-$, a carbonyl group, an alkylene group, an alkenylene group, an alkynylene group, $-C(=O)-X_1-$ or $-X_1-C(=O)-$, where the $X_1$ represents an oxygen atom, a sulfur atom, $-S(=O)_2-$, an alkylene group, an alkenylene group or an alkynylene group; and Y represents a monovalent substituent that includes a ring structure to which a chain with 8 or more chain-forming atoms is connected.

In the present application, the term "a single bond" may refer to an absence of any particular atom in the corresponding area. For example, in the case that the X of Structural Formula 1 represents a single bond, a structure having the Y connected directly to the polymer chain can be realized.

Unless specifically indicated otherwise, the term "an alkyl group" in the present specification may refer to a linear-type, branched-type or ring-type alkyl group with 1 to 20 carbons, 1 to 16 carbons, 1 to 12 carbons, 1 to 8 carbons or 1 to 4 carbons, which may be optionally substituted in part by one or more substituents (however, when the aforementioned side chain refers to an alkyl group, the alkyl group may contain 8 or more, 9 or more, 10 or more, 11 or more or 12 or more carbon atoms, where the number of carbon atoms in the alkyl group may also be 30 or less, 25 or less, 20 or less, or 16 or less).

Unless specifically indicated otherwise, the term "an alkenyl group" or "an alkynyl group" in the present specification may refer to a linear-type, branched-type or ring-type alkenyl group or alkynyl group with 2 to 20 carbons, 2 to 16 carbons, 2 to 12 carbons, 2 to 8 carbons or 2 to 4 carbons, which may be optionally substituted in part by one or more substituents (however, the alkenyl group or alkynyl group as the aforementioned side chain may contain 8 or more, 9 or more, 10 or more, 11 or more or 12 or more carbon atoms, where the number of carbon atoms in the alkenyl group or alkynyl group may also be 30 or less, 25 or less, 20 or less, or 16 or less).

Unless specifically indicated otherwise, the term "an alkylene group" in the present specification may refer to a linear-type, branched-type or ring-type alkylene group with 1 to 20 carbons, 1 to 16 carbons, 1 to 12 carbons, 1 to 8 carbons or 1 to 4 carbons, which may be optionally substituted in part by one or more substituents.

Unless specifically indicated otherwise, the terms "an alkenylene group" or "an alkynylene group" in the present specification may refer to a linear-type, branched-type or ring-type alkenylene group or alkynylene group with 1 to 20 carbons, 1 to 16 carbons, 1 to 12 carbons, 1 to 8 carbons or 1 to 4 carbons, which may be optionally substituted in part by one or more substituents.

In another example, the X of Structural Formula 1 may also represent —C(=O)O— or —OC(=O)—.

The Y of Structural Formula 1 represents a substituent that contains the aforementioned chain may be, for example, a substituent that includes an aromatic structure with 6 to 18 carbons or 6 to 12 carbons. The above chain may be, for example, a linear-chain alkyl group with 8 or more, 9 or more, 10 or more, 11 or more or 12 or more carbon atoms. The alkyl group may also contain 30 or less, 25 or less, 20 or less or 16 or less carbon atoms. The above chain may be connected to the above aromatic structure either directly or by an aforementioned linker.

In another example, the block 1 may be represented by the following Structural Formula 2.

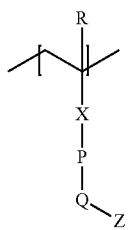

[Structural Formula 2]

In Structural Formula 2, R represents a hydrogen atom or an alkyl group with 1 to 4 carbons, X represents —C(=O)—O—, P represents an arylene group with 6 to 12 carbons, Q represents an oxygen atom, and Z represents an aforementioned chain with 8 or more chain-forming atoms.

In another example, the P of Structural Formula 3 may represent phenylene, and, in another example, the Z may represent a linear-chain alkyl group with 9 to 20 carbons, 9 to 18 carbons, or 9 to 16 carbons. When the P represents phenylene, the Q may be connected in the para position of the above phenylene. The above alkyl group, arylene group, phenylene group and chain may be optionally substituted in part by one or more substituents.

When a block copolymer contains a block that includes an aromatic structure with one or more halogen atoms, the block may be, for example, a block that is represented by the following Structural Formula 3.

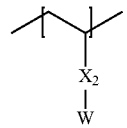

[Structural Formula 3]

In Structural Formula 3, $X_2$ represents a single bond, an oxygen atom, a sulfur atom, —S(=O)$_2$—, an alkylene group, an alkenylene group, an alkynylene group, —C(=O)—$X_1$— or —$X_1$—C(=O)—, where the $X_1$ represents a single bond, an oxygen atom, a sulfur atom, —S(=O)$_2$—, an alkylene group, an alkenylene group or an alkynylene group; and W represents an aryl group with at least one halogen atom.

In another example, the $X_2$ of Structural Formula 3 may represent a single bond or an alkylene group.

In Structural Formula 3, the aryl group that is represented by W may be an aryl group with 6 to 12 carbons or a phenyl group, where the aryl group or phenyl group may contain 1 or more, 2 or more, 3 or more, 4 or more or 5 or more halogen atoms. The number of the halogen atoms may also be, for example, 30 or less, 25 or less, 20 or less, 15 or less, or 10 or less. For the halogen atom, a fluorine atom may be exemplified.

In another example, the block that is represented by Structural Formula 3 may also be represented by the following Structural Formula 4.

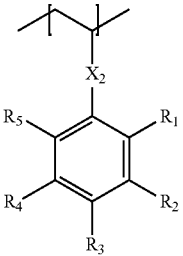

[Structural Formula 4]

In Structural Formula 4, $X_2$ is as defined in Structural Formula 2, and each of $R_1$ to $R_5$ independently represents a hydrogen atom, an alkyl group, a haloalkyl group or a halogen atom, where 1 or more halogen atoms are contained in the positions marked as $R_1$ to $R_5$.

In Structural Formula 4, each of $R_1$ to $R_5$ independently represents a hydrogen atom, an alkyl group with 1 to 4 carbons, a haloalkyl group with 1 to 4 carbons, or a halogen, where the halogen may be chlorine or fluorine.

In Structural Formula 4, 2 or more, 3 or more, 4 or more, 5 or more or 6 or more among $R_1$ to $R_5$ may each represent a halogen. There is no particular limitation to the maximum number of the above halogen; it may be, for example, 12 or less, 8 or less, or 7 or less.

The block copolymer may be a copolymer that contains either one or both of the above two types of blocks, either exclusively or together with other type(s) of block(s).

There is no particular limitation to the method of preparing a block copolymer. A block copolymer may be polymerized, for example, by a living radical polymerization (LRP) method, examples of which include synthesis by anionic polymerization in which an organic rare-earth metal complex or organic alkali metal compound is used as the polymerization initiator in the presence of an alkali metal and an inorganic acid salt such as an alkaline earth metal; synthesis by an anionic polymerization method in which an organic alkali metal compound is used as the polymerization initiator in the presence of an organic aluminum compound; an atom transfer radical polymerization (ATRP) method in which an ATRP agent is used as the polymerization-control agent; an activators regenerated by electron transfer (ARGET) ATRP method in which an ATRP agent is used as the polymerization-control agent but the polymerization takes place in the presence of an organic or inorganic reducing agent that generates an electron; an initiators for continuous activator regeneration (ICAR) ATRP method; polymerization by a reversible addition-fragmentation chain transfer (RAFT) for which an inorganic reducing agent and a RAFT agent are used; and a method of using an organic tellurium compound as the initiator, among which a suitable method may be selected for use.

For example, the aforementioned block copolymer may be prepared through polymerization of a reactant (that includes the monomers capable of forming the aforementioned block) by a living radical polymerization method in the presence of a radical initiator and a living radical polymerization reagent. The process of preparing a block copolymer may further include, for example, precipitating, in a nonsolvent, the polymerization product that is produced through the above processes.

There is no particular limitation to the type of the radical initiator, and the radical initiator may be suitably selected in consideration of the polymerization efficiency; for example, an azo compound such as azobisisobutyronitrile (AIBN) and 2,2'-azobis-(2,4-dimethylvaleronitrile), or a peroxide series such as benzoyl peroxide (BPO) and di-t-butyl peroxide (DTBP) may be used.

A living radical polymerization process may be carried out, for example, in a solvent such as methylene chloride, 1,2-dichloroethane, chlorobenzene, dichlorobenzene, benzene, toluene, acetone, chloroform, tetrahydrofuran, dioxane, monoglyme, diglyme, dimethylformamide, dimethyl sulfoxide, and dimethylacetamide.

Examples of a nonsolvent include, but are not limited to, an alcohol (such as methanol, ethanol, n-propanol, and isopropanol), a glycol (such as ethylene glycol), n-hexane, cyclohexane, n-heptane, and an ether (such as petroleum ether).

The present application also relates to a polymer film that contains the aforementioned block copolymer. The polymer film may be used in a variety of applications, for example, in a variety of electronic or electrical devices, in the process of forming the aforementioned patterns, in magnetic storage recording media such as flash memory, or in biosensors.

In one example, the aforementioned block copolymer may realize a regular structure, such as a cylinder, through self-assembly in the aforementioned polymer film. For example, the block 1, the block 2 or (in the segment of the other block that is covalently bonded to any of the block 1 and block 2) the segment may form a regular structure such as a cylindrical form in a block copolymer.

The present application also relates to a method of forming a polymer film by using the aforementioned block copolymer. The method may include forming a polymer film containing the above block copolymer on a substrate in a self-assembled state. For example, the above method may include depositing the above block copolymer, or a coating solution containing the block copolymer, to form a layer and then annealing the layer. The above annealing process may refer to a thermal annealing process or a solvent annealing process.

The above thermal annealing may be carried out, for example, based on the phase transition temperature or glass transition temperature of the block copolymer; for example, it may be carried out at a temperature equal to or greater than the above glass transition temperature or phase transition temperature. The duration of such thermal annealing is not particularly limited and may be, for example, in the range of about 1 minute to 72 hours, although it may be subject to change as necessary. Also, the heat-treatment temperature during a thermal annealing process may be, for example, about 100° C. to 250° C., which may be subject to change depending on the block copolymer to be used.

The above solvent annealing process may be carried out in a suitable room-temperature nonpolar solvent and/or polar solvent for about 1 minute to 72 hours.

The present application also relates to a method of forming a pattern. The above method may include, for example, a process of selectively removing the block 1 or block 2 of a block copolymer from the laminate that is made up of a substrate and a polymer film, which is formed on the substrate and contains the above self-assembled block copolymer. The above method may be a method of forming a pattern on the above substrate. For example, the above method may include forming, on a substrate, a polymer film that contains the above block copolymer, selectively removing any one or more blocks of the block copolymer that is present in the above film, and subsequently etching the substrate. The above method enables the formation of a micropattern, for example, in nanoscale. Also, a variety of patterns such as a nanorod and a nanohole may be formed by the above method, depending on the structure of the block copolymer in the polymer film. If needed, the above block copolymer may be mixed with another copolymer, a homopolymer or the like for the formation of patterns. The type of the substrate to be applied in the above method is not particularly limited and may be selected to suit the application; for example, silicon oxide may be used.

For example, the above method may form a silicon-oxide nanoscale pattern that exhibits a high aspect ratio. A variety of forms such as a nanorod and a nanohole may be realized, for example, by forming the above polymer film on the silicon oxide, selectively removing any one block of a block copolymer in the above polymer film where the block copolymer constitutes a predetermined structure, and then etching the silicon oxide by any one of various techniques, for example, by reactive-ion etching. Also, the above method may enable the realization of a nanopattern having a high aspect ratio.

For example, the above pattern may be realized in the scale of tens of nanometers, and such a pattern may be used for a variety of applications including, for example, magnetic recording media for the next-generation information and electronics.

For example, a pattern in which nanostructures (e.g. nanowires) whose width is about 10 nm to 40 nm are arranged spaced apart (e.g. by 20 nm to 80 nm) can be formed by the above method. In another example, a structure in which nanoholes whose width (e.g. diameter) is about 10 nm to 40 nm are arranged spaced apart by about 20 nm to 80 nm can also be realized.

In addition, the nanowires or nanoholes in the above structure can be made to have high aspect ratios.

In the above method, there is no particular limitation to the method of selectively removing any one block of a block copolymer; for example, a method of removing a relatively soft block by having the polymer film irradiated with suitable electromagnetic waves such as ultraviolet rays may be used. In this case, the condition of an ultraviolet ray irradiation is determined by the type of blocks in the block copolymer; for example, it may include an irradiation of the ultraviolet rays whose wavelength is about 254 nm for 1 minute to 60 minutes.

Following the ultraviolet ray irradiation, the process of additionally removing the segment that was previously disintegrated by ultraviolet rays may be carried out by treating the polymer film with an acid or the like.

There is no particular limitation to the process of etching the substrate by using, as the mask, the polymer film that has been selectively removed of certain blocks; for example, the above etching may be carried out through reactive-ion etching with $CF_4/Ar$ ions or the like. The above etching may be followed by the process of removing the polymer film from the substrate through an oxygen plasma treatment or the like.

BRIEF DESCRIPTION OF THE DRAWINGS

Each of FIGS. 1 to 4 is an NMR spectrum of a block copolymer of an example or comparative example.

Each of FIGS. 5 to 7 is an AFM or SEM image of a self-assembled film of a block copolymer of an example or comparative example.

EFFECT

Figure 1:
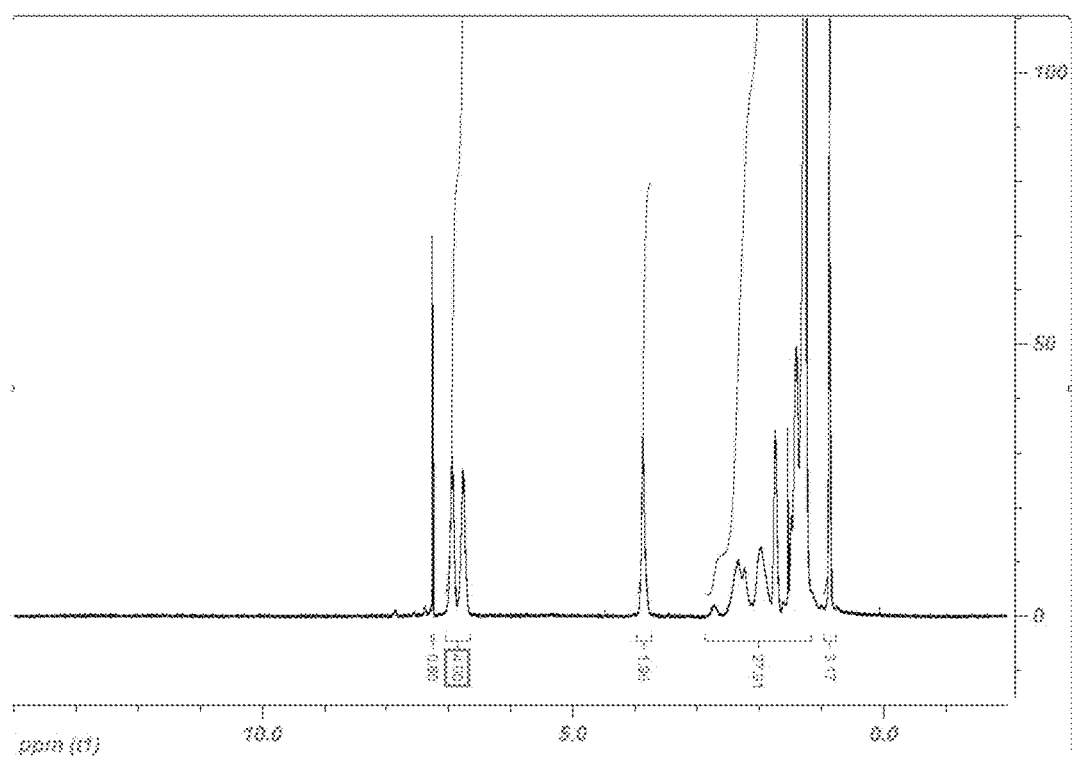

The present application can provide a block copolymer—which exhibits an excellent self-assembling property or phase separation property and, thus, can be used effectively in a variety of applications—and uses thereof.

DETAILED DESCRIPTION OF EXEMPLARY EMBODIMENTS

The present application is described in more detail hereinafter through examples according to the present application, but the scope of the present application is not limited to the examples which are proposed hereinafter.

1. NMR Measurement

NMR analysis was carried out at room temperature by using a NMR spectrometer that includes a Varian Unity Inova (500 MHz) spectrometer with a 5-mm triple resonance probe. The analysis subject material was diluted with a solvent ($CDCl_3$) for an NMR measurement to a concentration of about 10 mg/ml for use, and the chemical shift was expressed in ppm.

<Applied Abbreviations> br=broad signal, s=singlet, d=doublet, dd=doublet of doublets, t=triplet, dt=doublet of triplets, q=quartet, p=quintet, m=multiplet.

2. Gel Permeation Chromatography (GPC)

The number average molecular weight (Mn) and molecular weight distribution were measured by GPC. The analysis subject material such as a macroinitiator or the block copolymer of the examples was put in a 5-mL vial and diluted with tetrahydrofuran (THF) to a concentration of about 1 mg/mL. Then, a standard specimen for calibration and the specimen to be analyzed were filtered with a syringe filter (pore size: 0.45 μm) and subsequently analyzed. ChemStation (Agilent Technologies Inc.) was used as the analytical program, each of the weight average molecular weight (Mw) and Mn was obtained by comparing the elution time of the specimen with the calibration curve, and then a molecular weight distribution (polydispersity index, PDI) was calculated as a ratio (Mw/Mn). The measuring condition of GPC is as follows:

<GPC Measuring Conditions>

Device: 1200 Series of Agilent Technologies Inc.
Column: Two PLgel MIXED-B of Polymer Laboratories
Solvent: THF
Column temperature: 35° C.
Sample concentration: 1 mg/mL, 200 L is injected
Standard specimen: polystyrene (Mp: 3900000, 723000, 316500, 52200, 31400, 7200, 3940, 485)

3. Measurement of X by Equation 1

Each of the variables of Equation 1—D, M, K and L—can be obtained as follows:

First of all, D can be obtained by putting a specimen to be analyzed (i.e. a homopolymer that is prepared with only the monomer that constitutes the block 1 or a homopolymer that is prepared with only the monomer that constitutes the block 2) in a solvent (i.e. ethanol) whose mass and density in air are known, obtaining the density of each block through the mass of the specimen, and calculating the ratio of the masses of different types of specimen.

Also, M can be obtained as the ratio of molar masses of monomers that make up blocks in a block copolymer. For example, in the case of each block copolymer of an example, the molar mass of the monomer of Preparation Example 1, which is the monomer that constitutes the block 1 that will be described below in the present specification, is 346.5 g/mol, the molar mass of pentafluorostyrene that constitutes the block 2 is 194.1 g/mol, and, from the ratio, the value of M can be calculated to be about 1.79.

In addition, L can be obtained as the ratio of number of hydrogen atoms in the monomers that make up blocks in a block copolymer. For example, in the case of each block copolymer of an example, the number of hydrogen atoms in the monomer of Preparation Example 1, which is the monomer that constitutes the block 1, is 34, the number of hydrogen atoms in pentafluorostyrene that constitutes the block 2 is 3, and, from the ratio, the value of L can be calculated to be about 11.3.

Lastly, K can be calculated through the area of a spectrum that is obtained by the aforementioned NMR analysis method. In this case, when the peaks—each of which is obtained from each block in a block copolymer—do not overlap each other, the area of the peak derived from each block is simply analyzed, and K can be obtained as the ratio of the peak areas.

Figure 8:
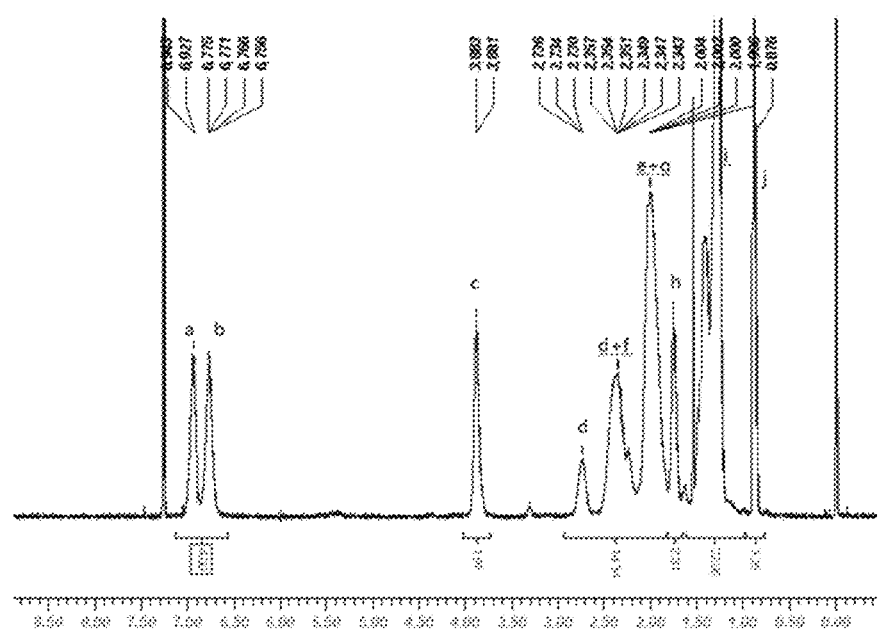
FIG. 8 is an image that illustrates an exemplary method for calculating the value of K of Equation 1.

In contrast, when the peaks derived from different blocks of a block copolymer overlap each other at least partly, the overlapped part should be taken into consideration when obtaining the value of K. For example, the accompanying FIG. 8 is an exemplary NMR spectrum of a block copolymer that contains a structural unit, which is derived from the compound represented by Structural Formula A that is prepared according to Preparation Example 1 and applied in the following examples and comparative example, and a structural unit derived from pentafluorostyrene. In FIG. 8, the part that is marked as e and the part that is marked as d refer to the peaks that come from the block 2 (that is, the aforementioned structural unit that is derived from pentafluorostyrene), and the rest (a, b, c, f, g, h, i and j) are the peaks that come from a structural unit that is derived from the compound (represented by Structural Formula A) of Preparation Example 1. As can be seen in the graph, the peaks marked as e and g and the peaks marked as d and f overlap each other; in which case, the overlapping of the peaks should be taken into consideration when obtaining the value of K.

In this case, the method of obtaining the value of K by taking the overlapping of the peaks into account is well known in the art; the value can be obtained, for example, by using an NMR interpretation program such as MestReC program.

PREPARATION EXAMPLE 1

Synthesis of Monomer A

The compound (DPM-C12) represented by the following Structural Formula A was synthesized by the following method: hydroquinone (10.0 g, 94.2 mmol) and 1-bromododecane (23.5 g, 94.2 mmol) were introduced into a 250-mL flask, dissolved in 100 mL of acetonitrile; then, an excessive amount of potassium carbonate was added to the above solution and allowed to react at about 75° C. for about 48 hours under a nitrogen atmosphere; upon completion of the reaction, the reaction products were filtered to be removed of the remaining potassium carbonate and acetonitrile that was used for the reaction; then the substances were worked up through an addition of a mixed solvent of dichloromethane (DCM) and water, and the separated organic layer was collected and dehydrated with $MgSO_4$; subsequently, the substances were purified by column chromatography (CC) with DCM to obtain a white solid target material (i.e. 4-(dodecyloxy)-phenol) with a yield of about 37%.

<NMR Analysis Results>
$^1$H-NMR ($CDCl_3$): δ6.77 (dd, 4H); δ4.45 (s, 1H); δ3.89 (t, 2H); δ1.75 (p, 2H); δ1.43 (p, 2H); δ1.33-1.26 (m, 16H); δ0.88 (t, 3H).

The synthesized 4-(dodecyloxy)-phenol (9.8 g, 35.2 mmol), methacrylic acid (6.0 g, 69.7 mmol), dicyclohexylcarbodiimide (DCC) (10.8 g, 52.3 mmol) and p-dimethylaminopyridine (DMAP) (1.7 g, 13.9 mmol) were introduced into a flask, 120 mL of methylene chloride was added, and then allowed to react at room temperature for 24 hours under a nitrogen atmosphere; upon completion of the reaction, the reaction products were filtered to be removed of a urea salt that was produced during the reaction and also of the remaining methylene chloride; then, the substances were removed of impurities by column chromatography (CC) that uses hexane and dichloromethane (DCM) as the mobile phase, the obtained products were recrystallized in a mixed solvent of methanol and water (mixed in a weight ratio of 1:1) to obtain a white solid target material (7.7 g, 22.2 mmol) with a yield of 63%.

<NMR Analysis Results>
$^1$H-NMR ($CDCl_3$): δ7.02 (dd, 2H); δ6.89 (dd, 2H); δ6.32 (dt, 1H); δ5.73 (dt, 1H); δ3.94 (t, 2H); δ2.05 (dd, 3H); δ1.76 (p, 2H); δ1.43 (p, 2H); 1.34-1.27 (m, 16H); δ0.88 (t, 3H).

[Structural Formula A]

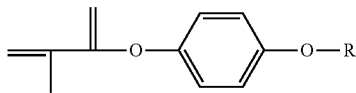

In Structural Formula A, R represents a linear-chain alkyl group with 12 carbons.

EXAMPLE 1

5.0 g of monomer A of Preparation Example 1, 165 mg of a reversible addition-fragmentation chain transfer (RAFT) reagent (cyanoisopropyl dithiobenzoate), 79 mg of a radical initiator (azobisisobutyronitrile, AIBN) and 11.9 mL of anisole were introduced into a 25-mL Schlenk flask, stirred at room temperature for 30 minutes under a nitrogen atmosphere, and then a RAFT polymerization reaction was carried out at 70° C. for 4 hours. Upon completion of the polymerization, the reaction solution was precipitated in 250 mL of an extraction solvent (methanol) and then dried by filtration under reduced pressure to prepare a pink macroinitiator. The yield of the macroinitiator was about 57.0 wt %, and the number average molecular weight (Mn) and molecular weight distribution (Mw/Mn) were 10300 and 1.21, respectively.

0.35 g of the above macroinitiator, 3.2 g of pentafluorostyrene (the monomer that constitutes the block 2) and 1.2 mL of anisole were introduced into a 10-mL Schlenk flask, stirred at room temperature for 30 minutes under a nitrogen atmosphere, and then a RAFT polymerization reaction was carried out at 115° C. for 4 hours. Upon completion of the polymerization, the reaction solution was precipitated in 250 mL of an extraction solvent (methanol) and then dried by filtration under reduced pressure to prepare a light-pink block copolymer. The yield of the block copolymer was about 13 wt %, and the Mn and Mw/Mn were 15,600 and 1.15, respectively. The above block copolymer contains the block 1 (that is derived from monomer A prepared according to Preparation Example 1) and the block 2 (that is derived from the aforementioned pentafluorostyrene monomer). The results of $^1$H-NMR analysis on the block copolymer that was prepared according to Example 1 are provided in FIG. 1.

EXAMPLE 2

Figure 2:
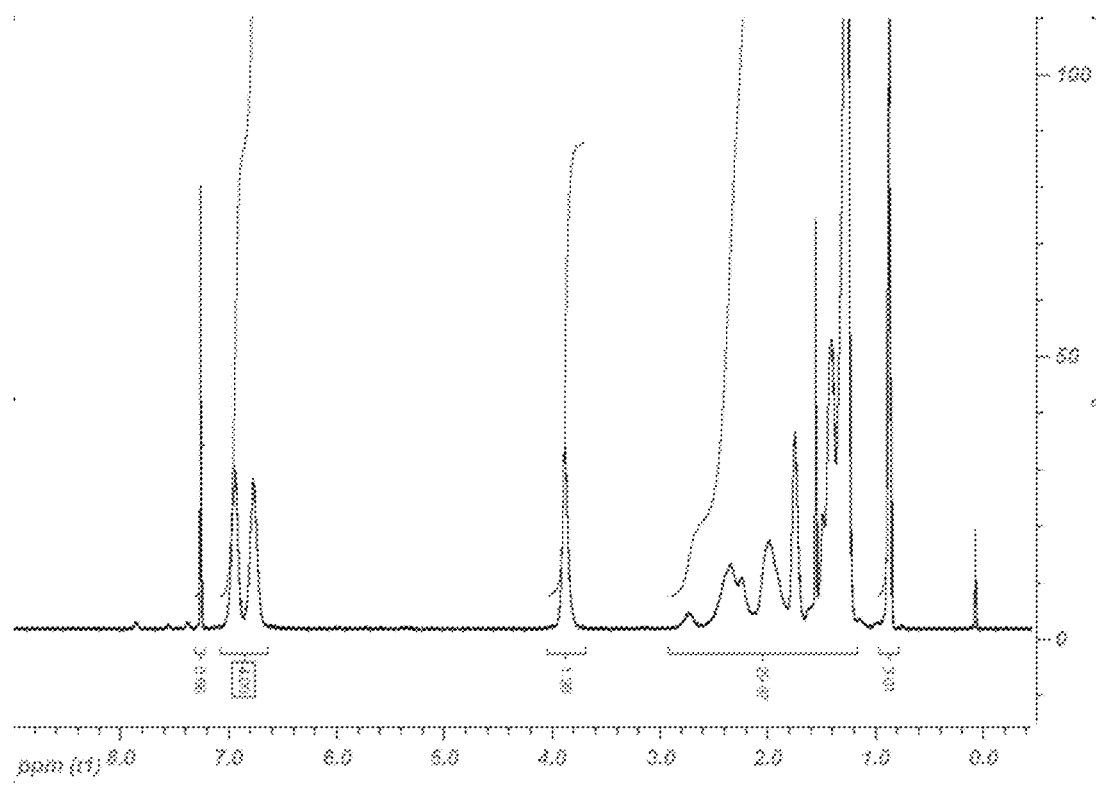

5.0 g of monomer A of Preparation Example 1, 106.5 mg of a reversible addition-fragmentation chain transfer (RAFT) reagent (cyanoisopropyl dithiobenzoate), 79 mg of a radical initiator (azobisisobutyronitrile, AIBN) and 11.9 mL of anisole were introduced into a 25-mL Schlenk flask, stirred at room temperature for 30 minutes under a nitrogen atmosphere, and then a RAFT polymerization reaction was carried out at 70° C. for 4 hours. Upon completion of the polymerization, the reaction solution was precipitated in 250 mL of an extraction solvent (methanol) and then dried by filtration under reduced pressure to prepare a pink macroinitiator. The yield of the macroinitiator was about 57.0 wt %, and the number average molecular weight (Mn) and molecular weight distribution (Mw/Mn) were 10,400 and 1.19, respectively. 0.3 g of the macroinitiator, 3.3 g of a pentafluorostyrene monomer and 1.2 mL of benzene were introduced into a 10-mL Schlenk flask, stirred at room temperature for 30 minutes under a nitrogen atmosphere, and then a RAFT polymerization reaction was carried out at 115° C. for 4 hours. Upon completion of the polymerization, the reaction solution was precipitated in 250 mL of an extraction solvent (methanol) and then dried by filtration under reduced pressure to prepare a light-pink block copolymer. The yield of the block copolymer was about 18 wt %, and the Mn and Mw/Mn were 17,800 and 1.14, respectively. The above block copolymer contains the block 1 (that is derived from monomer A prepared according to Preparation Example 1) and the block 2 (that is derived from the aforementioned pentafluorostyrene monomer). The results of $^1$H-NMR analysis on the block copolymer that was prepared according to Example 2 are provided in FIG. 2.

EXAMPLE 3

Figure 3:
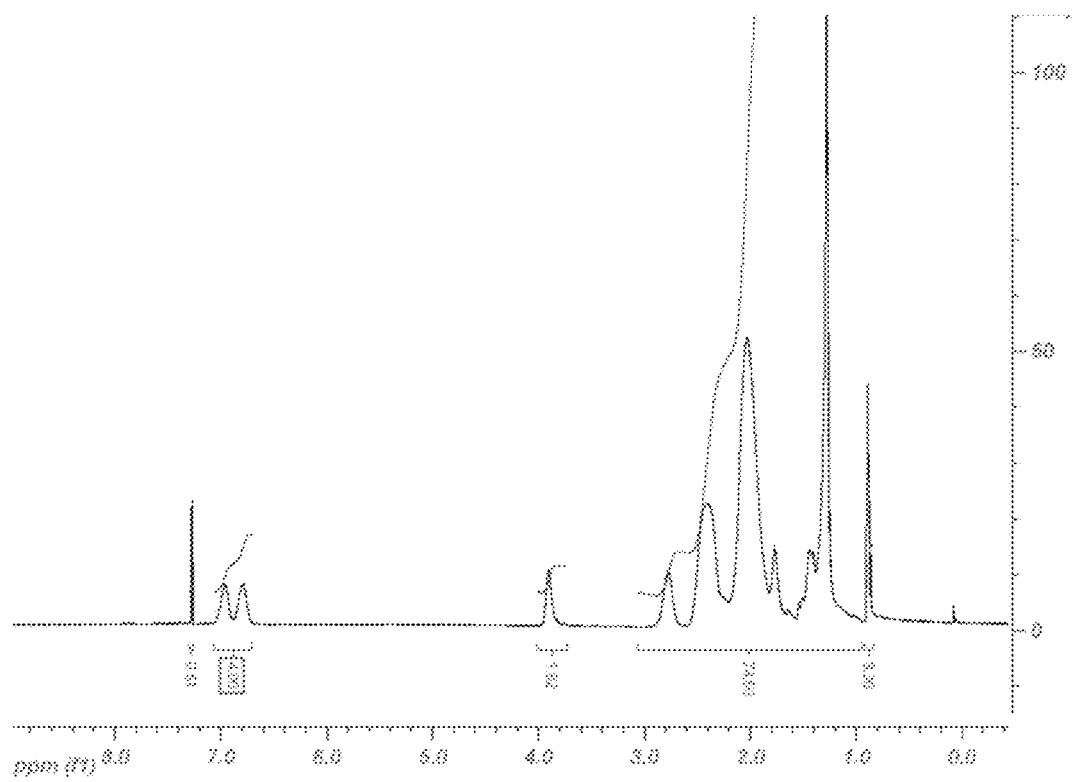

5.0 g of monomer A of Preparation Example 1, 456 mg of a reversible addition-fragmentation chain transfer (RAFT)

reagent (cyanoisopropyl dithiobenzoate), 34 mg of a radical initiator (azobisisobutyronitrile, AIBN) and 12.8 mL of anisole were introduced into a 25-mL Schlenk flask, stirred at room temperature for 30 minutes under a nitrogen atmosphere, and then a RAFT polymerization reaction was carried out at 70° C. for 4 hours. Upon completion of the polymerization, the reaction solution was precipitated in 250 mL of an extraction solvent (methanol) and then dried by filtration under reduced pressure to prepare a pink macroinitiator. The yield of the macroinitiator was about 60.0 wt %, and the number average molecular weight (Mn) and molecular weight distribution (Mw/Mn) were 5,700 and 1.18, respectively. 0.2 g of the macroinitiator, 3.4 g of a pentafluorostyrene monomer and 1.2 mL of anisole were introduced into a 10-mL Schlenk flask, stirred at room temperature for 30 minutes under a nitrogen atmosphere, and then a RAFT polymerization reaction was carried out at 115° C. for 15 hours. Upon completion of the polymerization, the reaction solution was precipitated in 250 mL of an extraction solvent (methanol) and then dried by filtration under reduced pressure to prepare a light-pink block copolymer. The yield of the block copolymer was about 16 wt %, and the Mn and Mw/Mn were 59,000 and 1.22, respectively. The above block copolymer contains the block 1 (that is derived from monomer A prepared according to Preparation Example 1) and the block 2 (that is derived from the aforementioned pentafluorostyrene monomer). The results of $^1$H-NMR analysis on the block copolymer that was prepared according to Example 3 are provided in FIG. 3.

COMPARATIVE EXAMPLE 1

Figure 4:
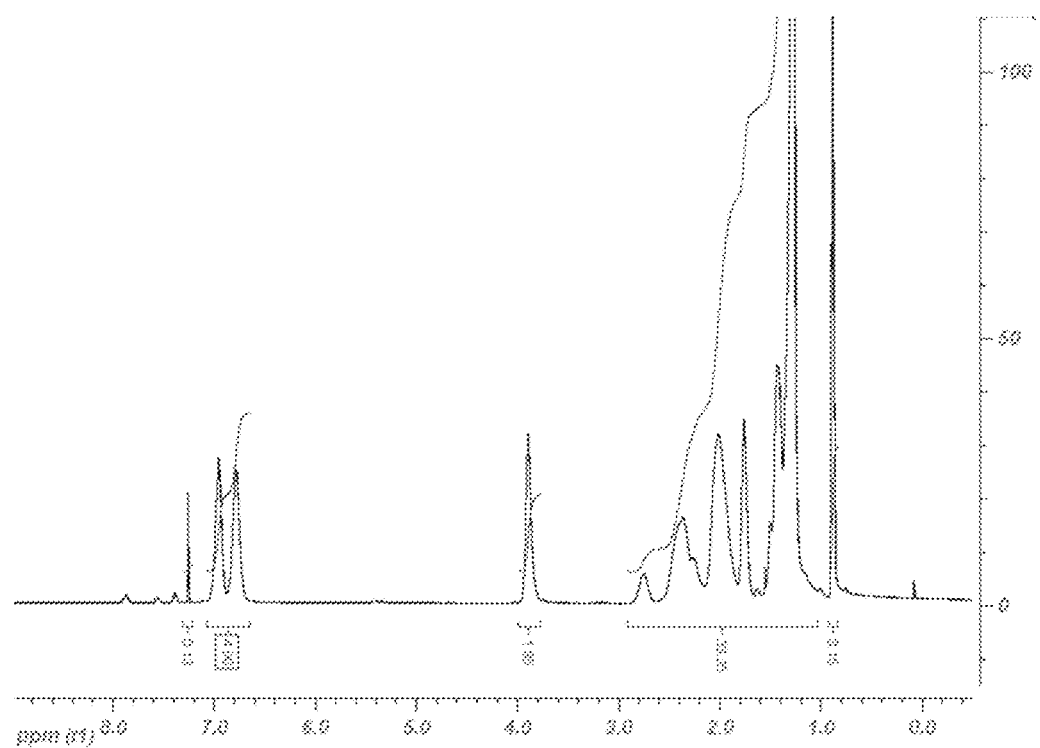

5.0 g of monomer A of Preparation Example 1, 106.5 mg of a reversible addition-fragmentation chain transfer (RAFT) reagent (cyanoisopropyl dithiobenzoate), 79 mg of a radical initiator (azobisisobutyronitrile, AIBN) and 11.9 mL of anisole were introduced into a 25-mL Schlenk flask, stirred at room temperature for 30 minutes under a nitrogen atmosphere, and then a RAFT polymerization reaction was carried out at 70° C. for 4 hours. Upon completion of the polymerization, the reaction solution was precipitated in 250 mL of an extraction solvent (methanol) and then dried by filtration under reduced pressure to prepare a yellow macroinitiator. The yield of the macroinitiator was about 52.0 wt %, and the number average molecular weight (Mn) and molecular weight distribution (Mw/Mn) were 9,100 and 1.20, respectively. 0.5 g of the macroinitiator, 4.5 g of a pentafluorostyrene monomer and 1.7 mL of anisole were introduced into a 10-mL Schlenk flask, stirred at room temperature for 30 minutes under a nitrogen atmosphere, and then a RAFT polymerization reaction was carried out at 115° C. for 4 hours. Upon completion of the polymerization, the reaction solution was precipitated in 250 mL of an extraction solvent (methanol) and then dried by filtration under reduced pressure to prepare a light-yellow block copolymer. The yield of the block copolymer was about 15 wt %, and the Mn and Mw/Mn were 23,200 and 1.12, respectively. The above block copolymer contains the block 1 (that is derived from monomer A prepared according to Preparation Example 1) and the block 2 (that is derived from the aforementioned pentafluorostyrene monomer). The results of $^1$H-NMR analysis on the block copolymer that was prepared according to Comparative Example 1 are provided in FIG. 4.

The measured results of GPC on each of the macroinitiators and block copolymers prepared according to the examples and comparative example are summarized and provided in Table 1 below, and each of the values of X of block copolymers prepared according to Examples 1 to 3 and Comparative Example 1 are summarized and provided in Table 2 below.

TABLE 1

|     |     | Examples | | | Comparative Example |
| --- | --- | --- | --- | --- | --- |
|     |     | 1 | 2 | 3 | 1 |
| MI  | Mn  | 10300 | 10400 | 5700 | 9100 |
|     | PDI | 1.21 | 1.19 | 1.18 | 1.20 |
| BCP | Mn  | 15600 | 17800 | 59000 | 23200 |
|     | PDI | 1.15 | 1.14 | 1.22 | 1.12 |

MI: macroinitiator
BCP: block copolymer
Mn: number average molecular weight
PDI: molecular weight distribution

TABLE 2

|         | Example 1 | Example 2 | Example 3 | Comparative Example 1 |
| --- | --- | --- | --- | --- |
| X value | 4 | about 3.2 | about 1.18 | 2 |
| D | 1.57 | 1.57 | 1.57 | 1.57 |
| M | about 1.79 | about 1.79 | about 1.79 | about 1.79 |
| K | about 0.08 | about 0.11 | about 1.37 | about 0.25 |
| L | about 11.3 | about 11.3 | about 11.3 | about 11.3 |

D: ratio (D2/D1) of density (D2) of block 2 to density (D1) of block 1
M: ratio (M1/M2) of molar mass (346.5 g/mol, M1) of monomer A of Preparation Example 1 (as monomer that constitutes block 1) to molar mass (194.1 g/mol, M2) of pentafluorostyrene (as monomer that constitutes block 2)
K: ratio (A2/A1) of area (A2) of peak in $^1$H-NMR produced based on block 2 to area (A1) of peak produced based on block 1
L: ratio (H1/H2) of number (34, H1) of hydrogen atoms in monomer A of Preparation Example 1 (as monomer that constitutes block 1) to number (3, H2) of hydrogen atoms in pentafluorostyrene (as monomer that constitutes block 2)

TEST EXAMPLE 1

Evaluation of Self-Assembling Property

Figure 5:
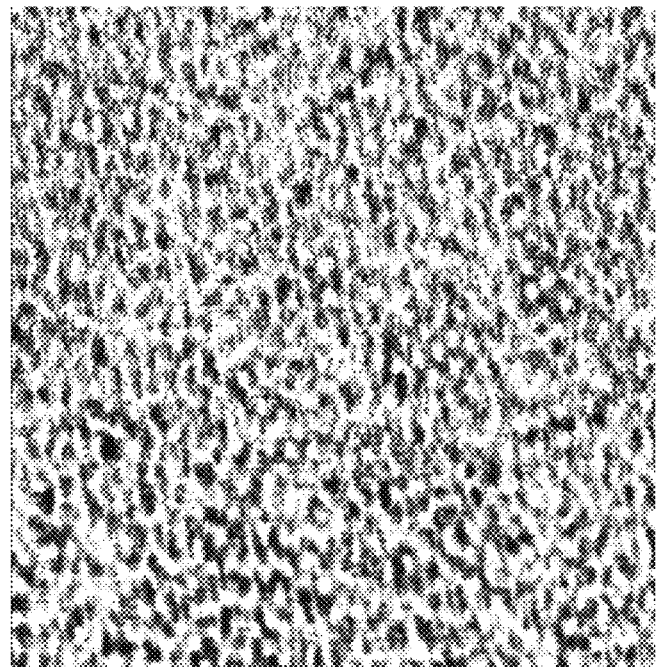
Figure 6:
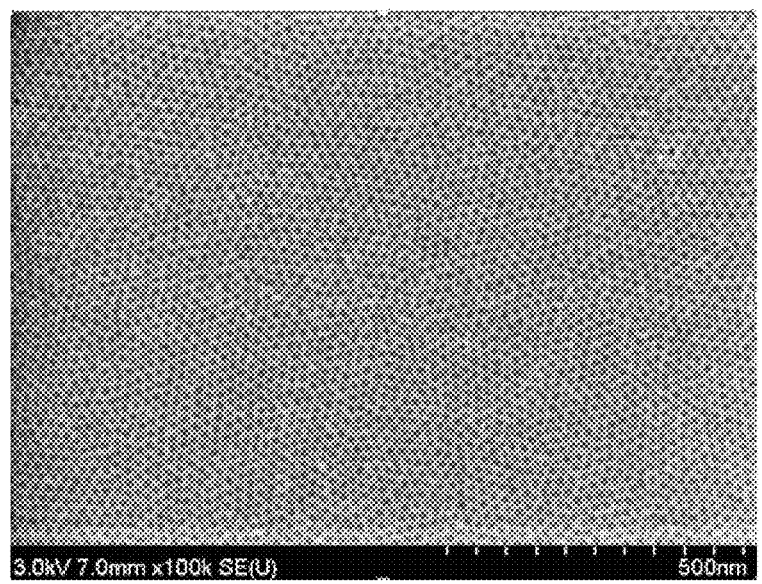
Figure 7:
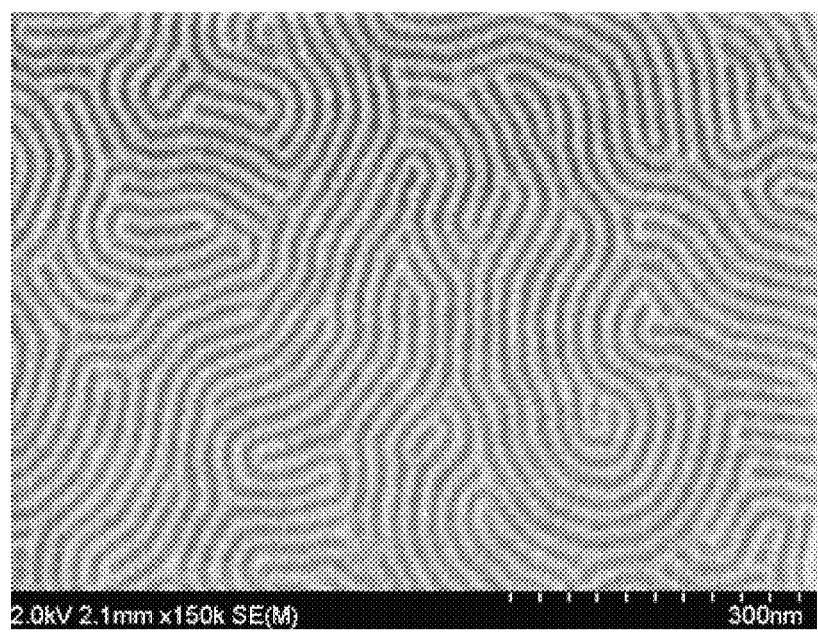

The coating solution prepared by dissolving the block copolymer of an example or comparative example in fluorobenzene to a solid concentration of 0.7 wt % was spin-coated (coating area: width×length=1.5 cm×1.5 cm) on a silicon wafer to a thickness of about 5 nm, dried at room temperature for about 1 hour, and then thermal-annealed at a temperature of about 160° C. for about 1 hour to form a self-assembled film. A scanning electron microscopic (SEM) image was taken of the film. FIG. 5 is an AFM image of Example 1, and FIG. 6 is an SEM image of Example 2. As seen in the images, a polymer film with a cylindrical structure was effectively formed with the block copolymer of Example, and a polymer film with a cylindrical structure was also observed with Example 3. In contrast, phase separation sufficient for the formation of a cylindrical structure was not induced with Comparative Example 1. FIG. 7 is the result of SEM of Comparative Example 1, from which a failure to induce effective phase separation into a cylindrical structure can be identified.

What is claimed is:
1. A block copolymer comprising a first block and a second block different from the first block, wherein X of Equation 1 below ranges from 2.5 to 10:

$$X = 1 + (D \times M)/(K \times L) \quad \text{[Equation 1]}$$

where in the Equation 1, D represents a ratio (D2/D1) of a density (D2) of the second block to a density (D1) of the first block;

M represents a ratio (M1/M2) of a molar mass (M1) of the first block to a molar mass (M2) of the second block;

K represents a ratio (A2/A1) in a $^1$H-NMR spectrum of an area (A2) of a peak that is produced based on the second block to an area (A1) of a peak that is produced based on the first block; and L represents a ratio (H1/H2) of a number (H1) of hydrogen atoms in 1 mole of a repeat unit of the first block to a number (H2) of hydrogen atoms in 1 mole of a repeat unit of the second block, wherein the first block includes an aromatic structure that connects to a main chain of the first block by a linker and the linker is an oxygen atom, a sulfur atom, —S(=O)$_2$—, a carbonyl group, an alkylene group, an alkenylene group, an alkynylene group,—C(=O)—X$_1$—or —X$_1$—C(=O)—, wherein the X$_1$ represents an oxygen atom, a sulfur atom, —S(=O)$_2$—, an alkylene group, an alkenylene group or an alkynylene group.

2. A block copolymer comprising a first block and a second block different from the first block, wherein X of Equation 1below ranges from 1.1 to 1.7:

$$X=1+(D \times M)/(K \times L) \quad \text{[Equation 1]}$$

where in the Equation 1, D represents a ratio (D2/D1) of a density (D2) of the second block to a density (D1) of the first block;

M represents a ratio (M1/M2) of a molar mass (M1) of the first block to a molar mass (M2) of the second block;

K represents a ratio (A2/A1) in a $^1$H-NMR spectrum of an area (A2) of a peak that is produced based on the second block to an area (A1) of a peak that is produced based on the first block; and L represents a ratio (H1/H2) of a number (H1) of hydrogen atoms in 1 mole of a repeat unit of the first block to a number (H2) of hydrogen atoms in 1 mole of a repeat unit of the second block, wherein the first block includes an aromatic structure that connects to a main chain of the first block by a linker and the linker is an oxygen atom, a sulfur atom, —S(=O)$_2$—, a carbonyl group, an alkylene group, an alkenylene group, an alkynylene group, —C(=O)—X$_1$—or —X$_1$—C(=O)—, wherein the X$_1$ represents an oxygen atom, a sulfur atom, —S(=O)$_2$—, an alkylene group, an alkenylene group or an alkynylene group.

3. The block copolymer of claim 1, wherein it forms a cylindrical structure.

4. The block copolymer of claim 1, wherein the second block includes an aromatic structure.

5. The block copolymer of claim 1, wherein the first block includes a side chain that is connected to the aromatic structure of the first block.

6. The block copolymer of claim 5, wherein the side chain is connected to the aromatic structure of the first block by an oxygen atom or a nitrogen atom.

7. The block copolymer of claim 1, wherein the first block includes a side chain that includes 8 or more chain-forming atoms.

8. The block copolymer of claim 1, wherein the first block includes a side chain that is connected to the aromatic structure of the first block, and the second block includes an aromatic structure that includes one or more halogen atoms.

9. The block copolymer of claim 1, wherein the first block includes a structural unit represented by Structural Formula 1 below:

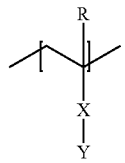

[Structural Formula 1]

where in the Structural Formula 1, R represents a hydrogen atom or an alkyl group with 1 to 4 carbons;

X represents an oxygen atom, a sulfur atom, —S(=O)$_2$—, a carbonyl group, an alkylene group, an alkenylene group, an alkynylene group, —C(=O)—X$_1$—or —X$_1$—C(=O)—, wherein the X$_1$ represents an oxygen atom, a sulfur atom, —S(=0)$_2$—, an alkylene group, an alkenylene group or an alkynylene group; and Y represents a monovalent substituent that includes an aromatic structure to which a side chain including 8 or more chain-forming atoms is connected.

10. The block copolymer of claim 1, wherein the second block includes a structural unit represented by Structural Formula 3 below:

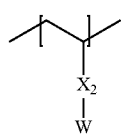

[Structural Formula 3]

where in the Structural Formula 3, X$_2$ represents a single bond, an oxygen atom, a sulfur atom, —S(=O)$_2$—, an alkylene group, an alkenylene group, an alkynylene group, —C(=O)—X$_1$—or —X$_1$—C(=O)—, wherein the X$_1$ represents a single bond, an oxygen atom, a sulfur atom, —S(=O)$_2$—, an alkylene group, an alkenylene group or an alkynylene group; and W represents an aryl group that includes at least one halogen atom.

11. The block copolymer of claim 1 having a number average molecular weight ranging from 3,000 to 300,000.

12. The block copolymer of claim 1 comprising a polydispersity (Mw/Mn) ranging from 1.01 to 1.60.

13. A polymer film comprising the block copolymer of claim 1, wherein the block copolymer is self-assembled.

14. A method of forming a polymer film comprising:
depositing the of claim 1 or coating the block copolymer of claim 1 on a substrate to form a layer, and
annealing the layer.

15. A method of forming a pattern, the method comprising:
forming a polymer film containing the block copolymer of claim 1 on a substrate, removing the first block or second block of the block copolymer from the polymer film, and
etching the substrate.

* * * * *